(12) United States Patent
Gannon

(10) Patent No.: US 11,500,197 B2
(45) Date of Patent: Nov. 15, 2022

(54) EFFICIENT OPTICAL SYSTEM DESIGN AND COMPONENTS

(71) Applicant: Arizona Board of Regents on Behalf of the University of Arizona, Tucson, AZ (US)

(72) Inventor: Caleb Daniel Gannon, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 0 days.

(21) Appl. No.: 17/054,717

(22) PCT Filed: May 10, 2019

(86) PCT No.: PCT/US2019/031744
§ 371 (c)(1),
(2) Date: Nov. 11, 2020

(87) PCT Pub. No.: WO2019/217832
PCT Pub. Date: Nov. 14, 2019

(65) Prior Publication Data
US 2021/0063730 A1 Mar. 4, 2021

Related U.S. Application Data

(60) Provisional application No. 62/670,571, filed on May 11, 2018.

(51) Int. Cl.
*G02B 27/00* (2006.01)
*A61B 3/10* (2006.01)
(Continued)

(52) U.S. Cl.
CPC ........ *G02B 27/0012* (2013.01); *A61B 3/1015* (2013.01); *G01B 11/255* (2013.01); *G01M 11/0264* (2013.01)

(58) Field of Classification Search
CPC .......... G02B 27/0012; G01M 11/0264; A61B 3/1015; G01B 11/255
See application file for complete search history.

(56) References Cited

U.S. PATENT DOCUMENTS 5,924,788 A 7/1999 Parkyn
6,038,387 A 3/2000 Machida
(Continued)

FOREIGN PATENT DOCUMENTS

WO WO-2017125902 A1 * 7/2017 ........ G01M 11/0207

OTHER PUBLICATIONS

Caleb Gannon, Using spherical harmonics to describe large-angle freeform lenses, Sep. 25, 2018, Applied Optics, vol. 57, No. 28, pp. 8143-8147 (Year: 2018).*

(Continued)

*Primary Examiner* — Michael P LaPage
(74) *Attorney, Agent, or Firm* — Perkins Coie LLP

(57) ABSTRACT

Methods, apparatus and systems for achieving efficient optical design are described. In one representative aspect, a method for optical design includes introducing a light source into the optical system. The light source emits illumination that is characterized as a point source, a collimated illumination, or a superposition of one or more point sources or one or more collimated illuminations. The light source is represented by a vector field comprising a plurality of vectors. The method also includes defining each optical surface of the optical system based on the vector field of the light source, tracing a plurality of rays that propagate from the light source, traverse through the optical system and reach a predetermined target or targets, and determining whether an illumination or an image characteristic at the predetermined target or targets meets preset design requirements.

10 Claims, 29 Drawing Sheets

(51) Int. Cl.
　　　*G01B 11/255*　　　(2006.01)
　　　*G01M 11/02*　　　(2006.01)

(56) References Cited

U.S. PATENT DOCUMENTS

| | | | |
|---|---|---|---|
| 6,496,253 B1 * | 12/2002 | Vokhmin | G01M 11/0264 |
| | | | 356/124 |
| 8,129,666 B2 | 3/2012 | Gross et al. | |
| 2005/0086032 A1 | 4/2005 | Benitez et al. | |

OTHER PUBLICATIONS

Gannon, Caleb, et al., "Spherical Harmonics For Freeform Illumination Design", College of Optical Sciences, University of Arizona, Optics Letters pp. 1-4.

Petrov, Yury. "Harmony: EEG/MEG linear inverse source reconstruction in the anatomical basis of spherical harmonics." PLoS one 7.10 (2012): e44439.

Solano-Altamirano, Juan Manuel, et al., "Using Spherical-Harmonics Expansions for Optics Surface Reconstruction from Gradients", MDPI, Sensors, 2017.

International Search Report and Written Opinion dated Sep. 5, 2019 for International Patent Application No. PCT/US2019/031744 (11 pages).

* cited by examiner

Vector Field - V

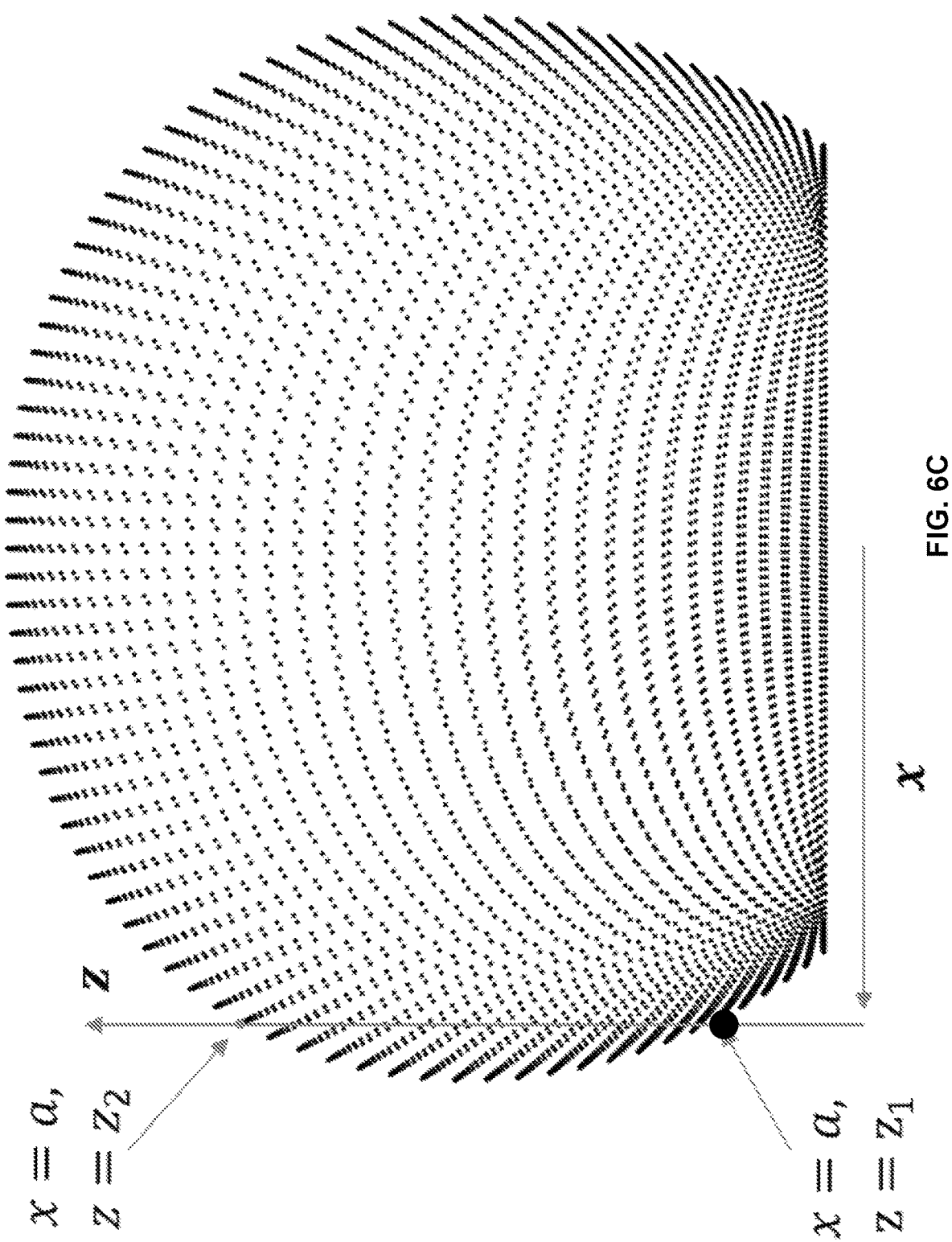

Vector Field - V

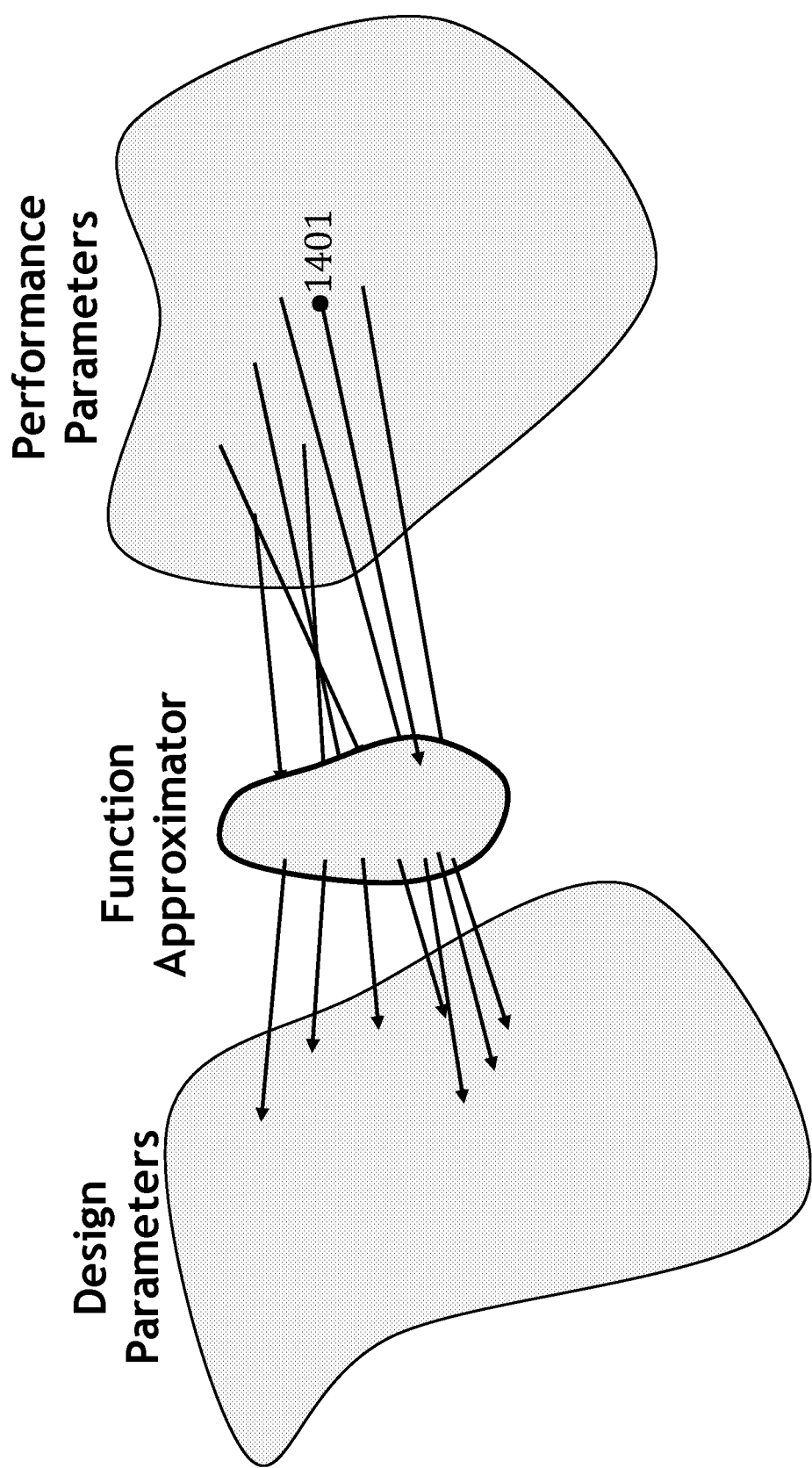

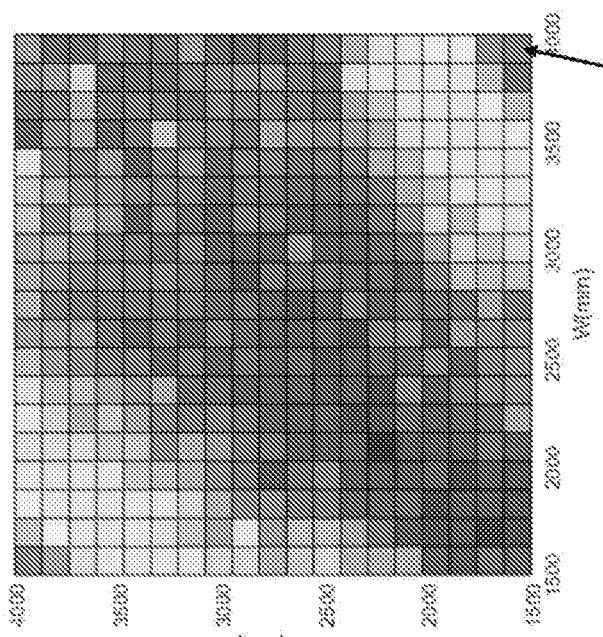
FIG. 16A
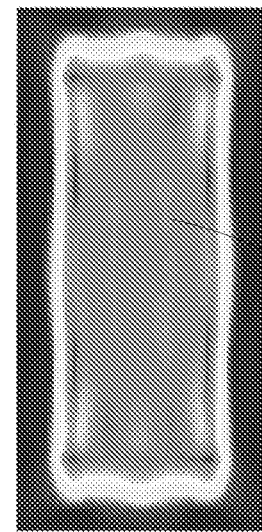
1631
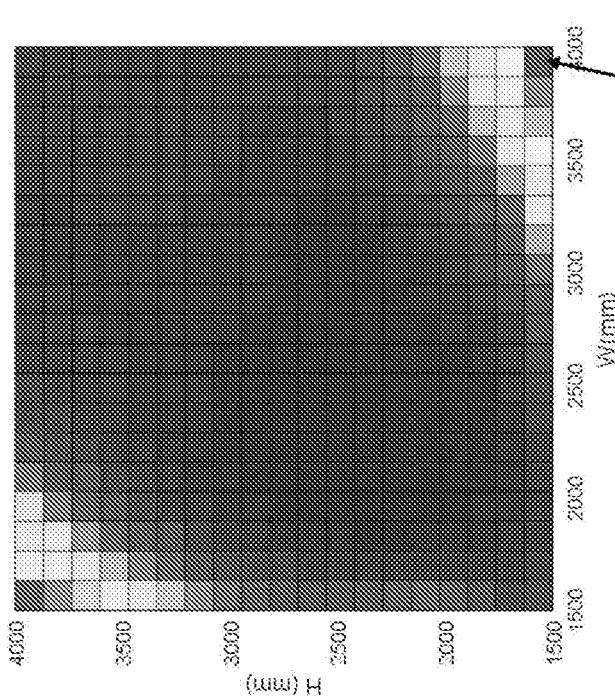
FIG. 16B
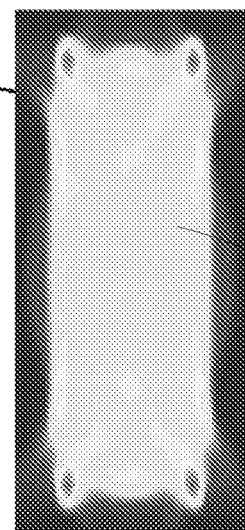
1651

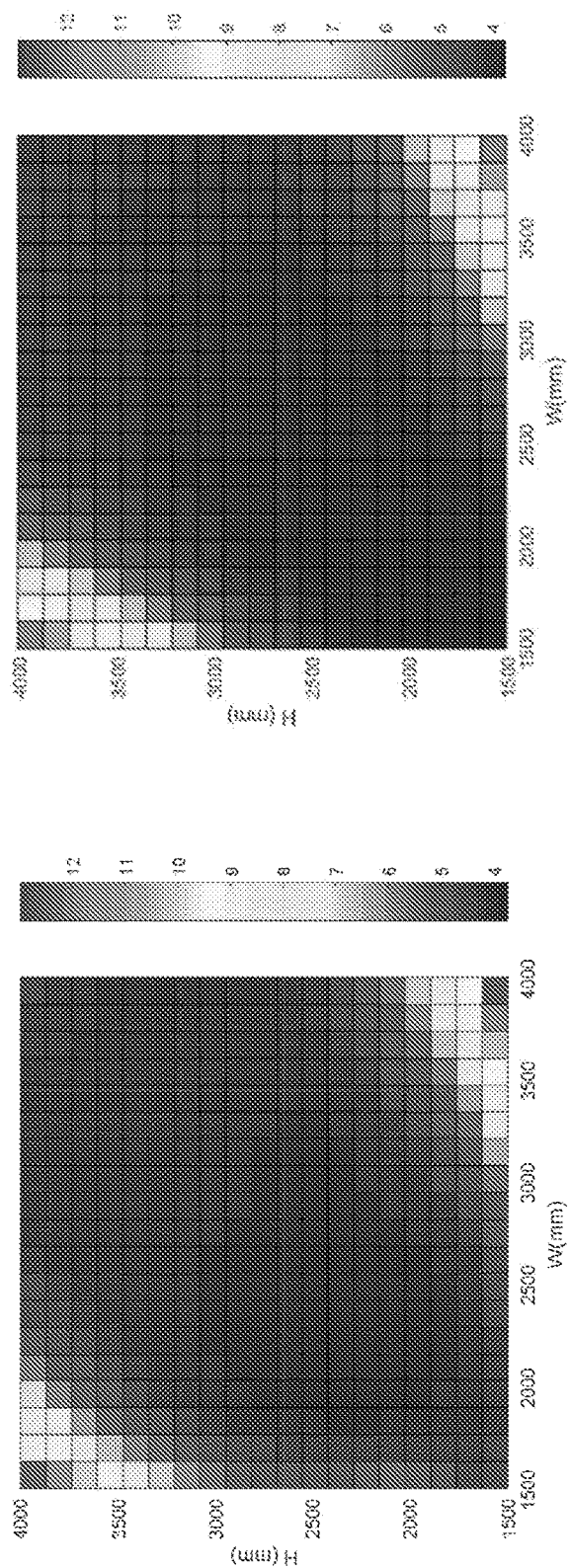
FIG. 17A
FIG. 17B
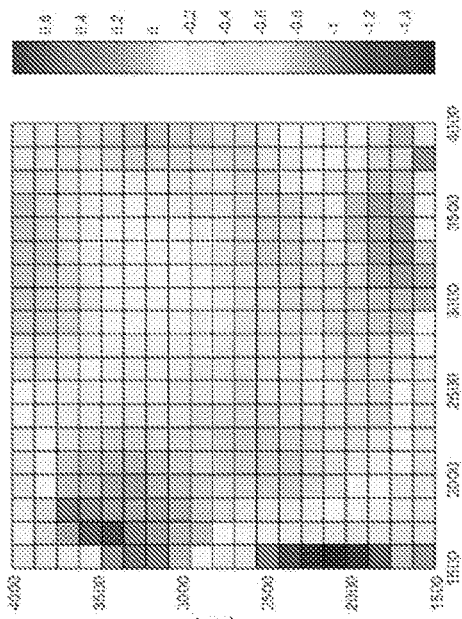
FIG. 17C

1900

positioning a light source and at least a lens in a first iteration of designing the optical system, wherein multiple rays from the light source are traced through the system, including multiple surfaces of the lens, before reaching a target area, and wherein the multiple rays are represented by a vector field comprising a plurality of vectors

1902 iterative performing, upon determining that an irradiance pattern formed by the light beams through the lens fails to meet one or more predetermined criteria for the target area, an optimization procedure

EFFICIENT OPTICAL SYSTEM DESIGN AND COMPONENTS

CROSS REFERENCE TO RELATED APPLICATIONS

This patent document is a 371 National Phase Application of International Patent Application No. PCT/US2019/031744, filed May 10, 2019, which claims priority to the U.S. Provisional application with Ser. No. 62/670,571, titled "EFFICIENT OPTICAL LENS DESIGN," filed May 11, 2018. The entire contents of the above noted applications are incorporated by reference as part of the disclosure of this document.

STATEMENT REGARDING FEDERALLY SPONSORED RESEARCH

This invention was made with government support under Grant No. DGE-1746060, awarded by NSF. The government has certain rights in the invention.

TECHNICAL FIELD

The disclosed embodiments relate to optical systems and in particular to design of optical systems and components therein.

BACKGROUND

Optical lens design is the process of designing a lens to meet a set of performance requirements and constraints. In physics, ray tracing is a method for calculating the path of waves or particles through a system with regions of varying propagation velocity, absorption characteristics, and reflecting surfaces. Ray tracing techniques have been widely used to design optical systems, but ray tracing operations are computationally expensive, which result in prolonged design processes to meet the performance requirements.

SUMMARY

The disclosed embodiments relate to methods, devices and systems that improve design of optical systems and optical components within those systems that are achieved in-part by using the incoming vector filed of light beam to represent the optical surface(s) to eliminate expensive computational steps. The disclosed technology finds numerous applications including, but not limited to, optical designs with a point light source or a collimated light source.

One aspect of the disclosed embodiments relates to a method for designing an optical system including a light source and a plurality of optical surfaces. The method includes introducing a light source into the optical system. The light source emits illumination that is characterized as a point source, a collimated illumination, or a superposition of one or more point sources or one or more collimated illuminations. The light source is represented by a vector field comprising a plurality of vectors. The method includes defining each optical surface of the optical system based on the vector field of the light source and tracing a plurality of rays that propagates from the light source, traverses through the optical system and reaches a predetermined target or targets. Each of the plurality of rays is represented based on the vector field of the light source upon reflection, refraction, or transmission through or from each optical surface of the optical system. The method also includes determining whether an illumination or an image characteristic at the predetermined target or targets meets preset design requirements.

Another aspect of the disclosed embodiments relates to positioning a light source and at least a lens in a first iteration of designing the optical system. Multiple rays from the light source are traced through the system, which includes multiple surfaces of the lens, before reaching a target area. The multiple rays are represented by a vector field comprising a plurality of vectors. The method includes iteratively performing, upon determining that an irradiance pattern formed at the target area fails to meet one or more predetermined criteria, an optimization procedure that comprises adjusting a characteristic of one or more surfaces of the lens. Each of the one or more surfaces of the lens is represented based on the vector field of the light source. The optimization procedure includes determining, for each ray, intersection points between the one or more surfaces of the lens and the corresponding ray based on the vector field and computing, for each ray, surface normal vectors corresponding to the intersection points. The surface normal vectors are represented based on the vector field of the light source. The optimization procedure also includes computing, for each ray, a trajectory of a refracted ray that exits the one or more surfaces based on the normal vectors and updating the irradiance pattern using the refracted rays.

BRIEF DESCRIPTION OF THE DRAWINGS

FIG. 6C illustrates an example of a one-to-many correspondence using a polynomial representation in Cartesian coordinates.

FIG. 14C illustrates a schematic diagram of determining a new set of design parameters based on a particular set of performance parameters in accordance with the disclosed technology.

FIG. 16A illustrates an example database of irradiance patterns produced by a neural network in accordance with disclosed technology prior to a training step.

FIG. 16B illustrates an example database of irradiance patterns produced by the neural network in accordance with disclosed technology after the training step.

FIG. 17A illustrates an example data base of irradiance patterns that is manually generated.

FIG. 17B illustrates an example database of irradiance patterns automatically generated by a trained neural network that maps between performance parameters to design parameters.

FIG. 17C illustrates a different between the databases shown in FIGS. 17A-17B.

FIG. 19 illustrates another flowchart representation of a method for optical design in accordance with the disclosed technology.

DETAILED DESCRIPTION

Ray tracing techniques have been used to design optical systems. Using these techniques, the paths of optical rays are computed as they propagate through the system with regions of varying propagation velocity, absorption characteristics, and reflecting surfaces. Typically, many rays (e.g., hundreds, thousands, or up to billions) are traced through the system that are varied by discrete amounts. The ray tracing operations are computationally expensive due to several factors, including the large number of rays that must be traced through the system, and the computations that are needed to run each trace through the system. The disclosed embodiments relate to methods and associated devices and systems that greatly reduce the computational operations of a ray tracing system that are achieved in-part by modifying the representations of the optical surfaces and contours in the optical system based on the illumination source, which can, for example, be a point source, a collimated source, or an extended source including a superposition of point sources or collimated sources. In the sections that follow, various figures are used to facilitate the understanding of the problems in existing ray tracing systems, and to illustrate example embodiments that provide vast improvements in efficiency and cost.

Figure 1:
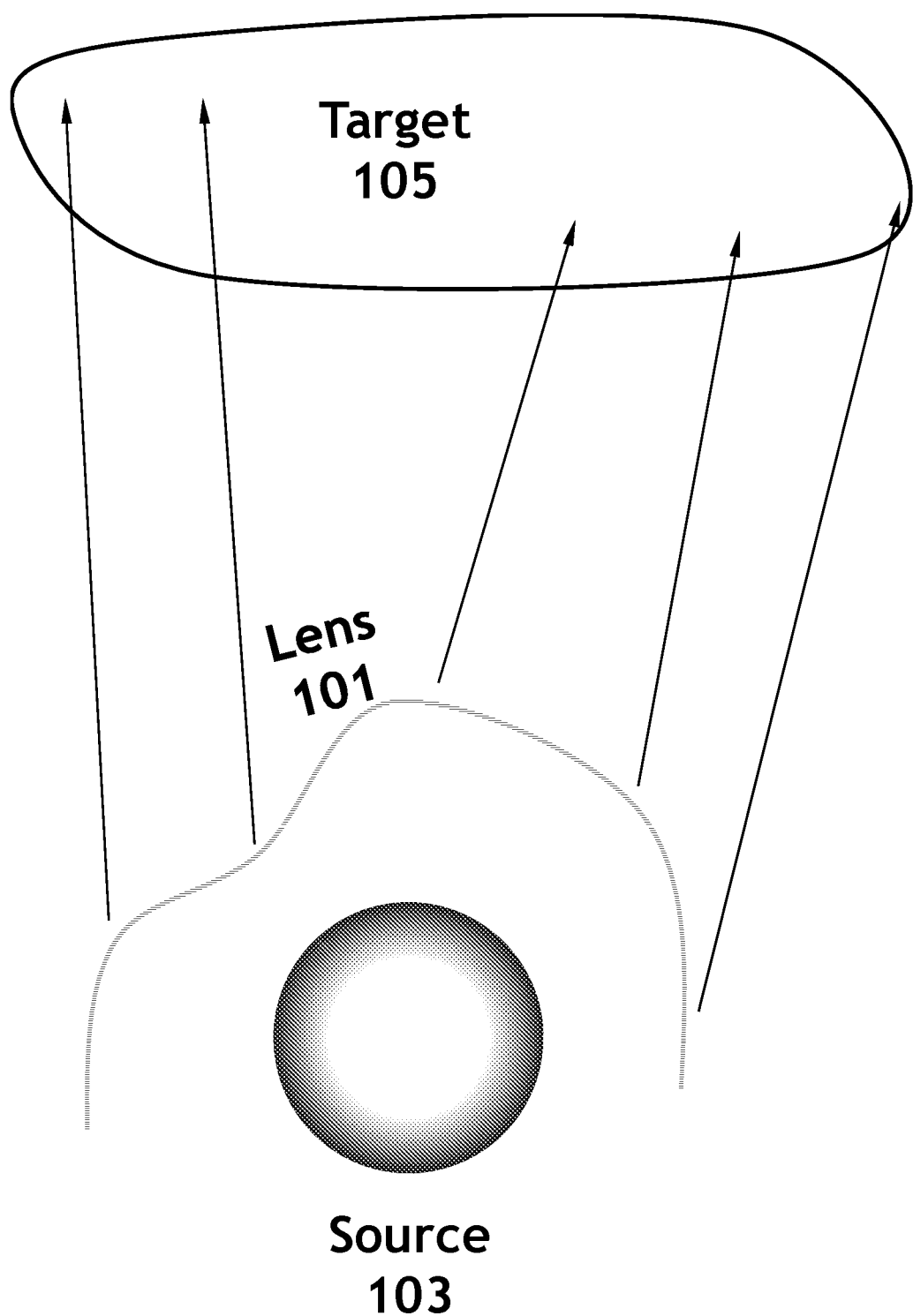
FIG. 1 is a schematic illustration of a representative optical design configuration.

FIG. 1 is a schematic illustration of a representative optical design configuration in which a source 103 with known characteristics is used to design a lens 101 that provides illumination onto a target 105 with certain uniformity, size and intensity characteristics. In this example, the lens 101 is positioned to encompass a light source 103. Design parameters of the lens 101 can include surface profiles, radius of surface curvature, distance to the next surface (e.g., a target area), material type, etc. These parameters are adjusted so that the light received at the target area 105 meets the set of performance requirements. As noted above, this design process is computationally intensive. To achieve the desired performance, many iterations are needed to determine a set of good design parameters.

Figure 2:
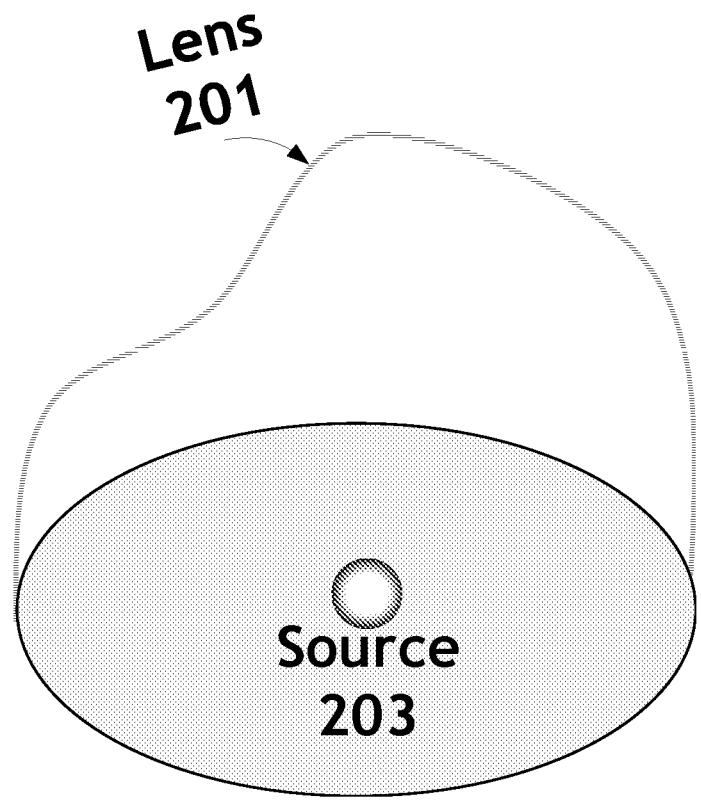
FIG. 2 illustrates an example of a surface representation of a lens.
Figure 3A:
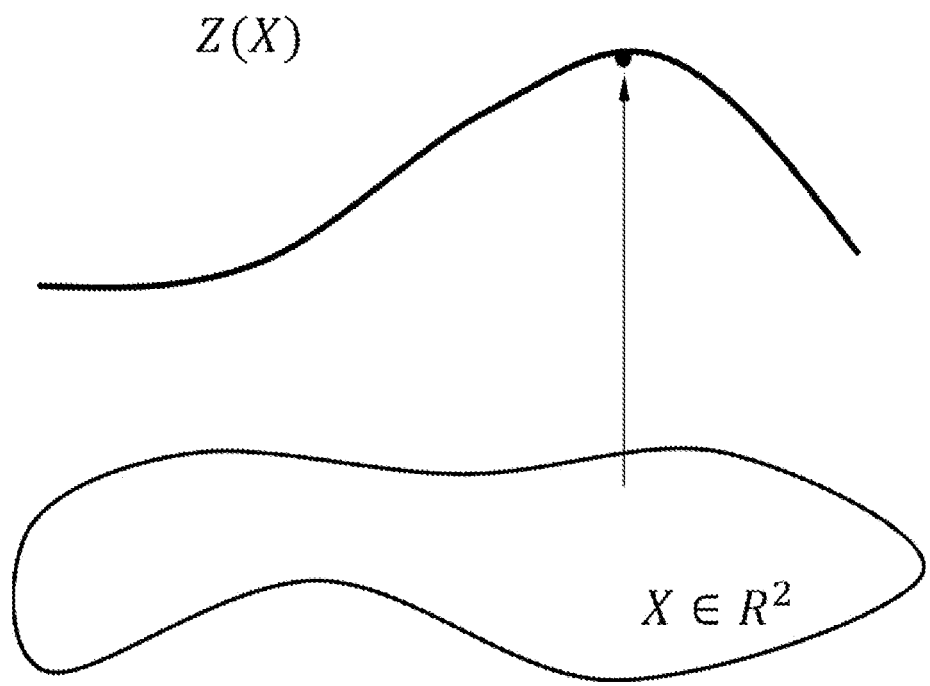
FIG. 3A is a schematic diagram showing a surface profile represented by Zernike polynomials.
Figure 3B:
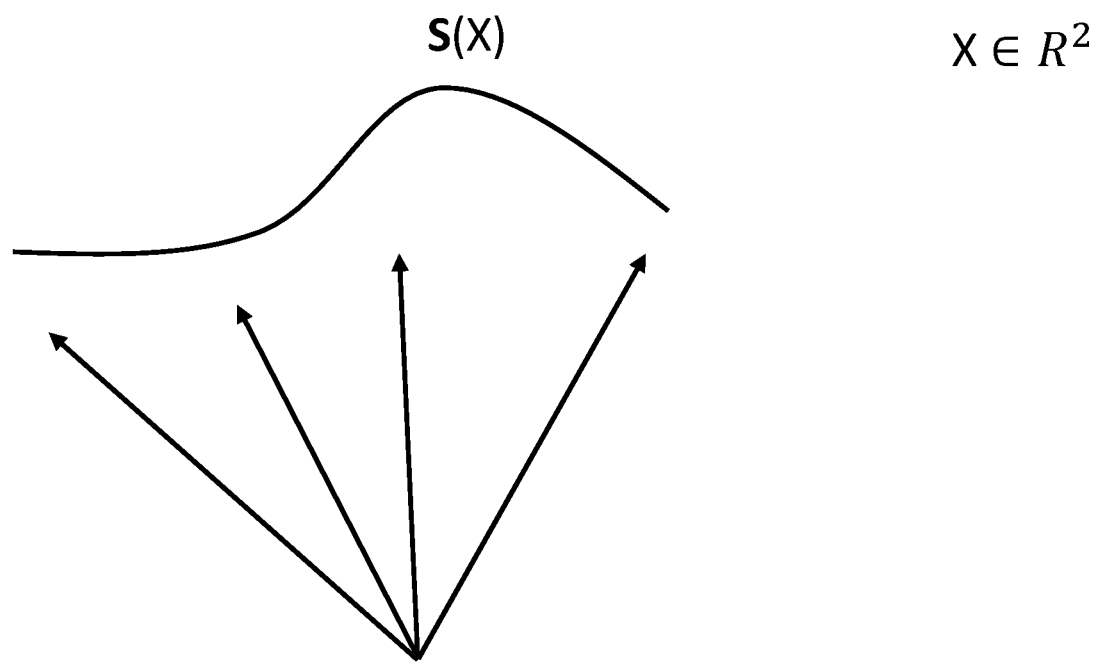
FIG. 3B illustrates a vector field of a point light source and a surface represented in the Cartesian coordinate system.

Many of the design parameters are related to the surface representation of the lens. FIG. 2 shows an example of a lens surface 201 that is positioned to encompass a light source 203. A lens surface is typically represented by functions (e.g., polynomials) in Cartesian coordinates. For example, FIG. 3A is a schematic diagram showing a surface profile represented by Zernike polynomials $Z(X)$, where $X \in R^2$. The light rays, on the other hand, are typically represented as a vector field, which may or may not be in Cartesian coordinates. FIG. 3B shows a vector field of a point source and a surface represented in Cartesian coordinates. The surface is represented by a function S(X) in Cartesian coordinates, where $X \in R^2$. The light rays are represented by the vector field V.

Figure 4A:
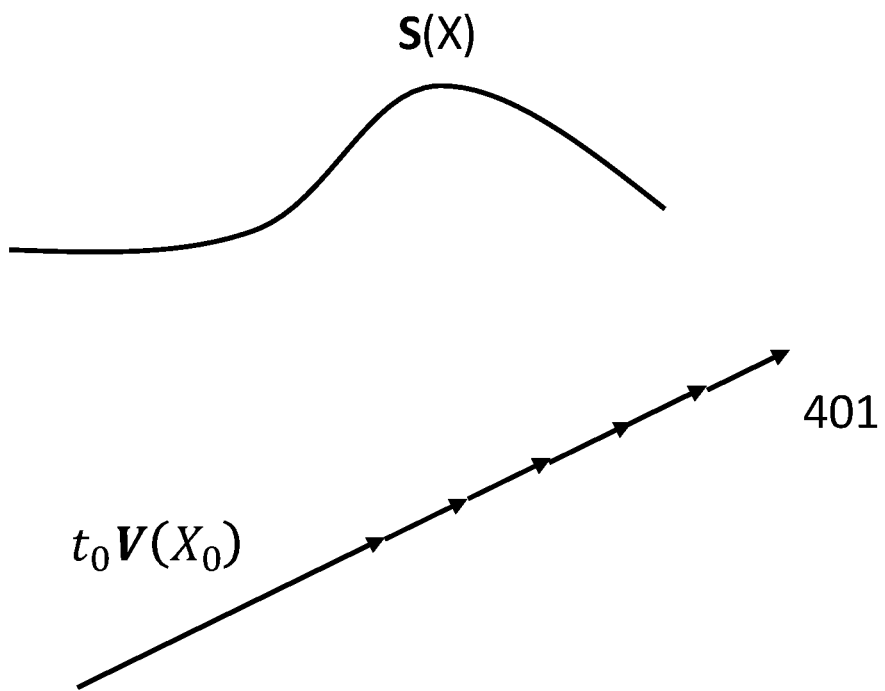
FIG. 4A illustrates an example of a light beam not intersecting with a surface.
Figure 4B:
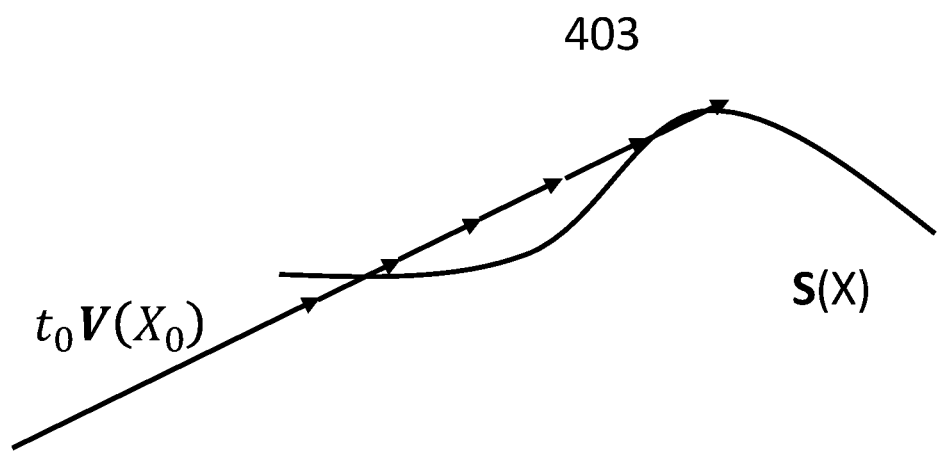
FIG. 4B illustrates an example of a light beam intersecting a surface twice.

Such representations, however, may not be effective for design processes that use ray tracing. Because the surface is represented by polynomials in Cartesian coordinates, a simple analytical solution for determining the point where a ray intersects the surface is not readily available. Therefore, the algorithm typically steps along the ray iteratively to obtain a numerical solution for the intersection point. However, as shown in FIG. 4A, a ray 401 may never intersect with the surface S(X), yet the algorithm would still step the ray multiple times to compute whether an intersection point exists. As another example shown in FIG. 4B, a ray 403 may intersect the surface S(X) multiple times. The additional optical effects (e.g., refraction and/or reflection) caused by multiple intersections along the ray may not be desirable for the lens surface. Furthermore, as the surface shape gets more irregular, the complexity of polynomial functions that are needed to represent the surface increases substantially, causing additional computational complexity for the design process.

Figure 5A:
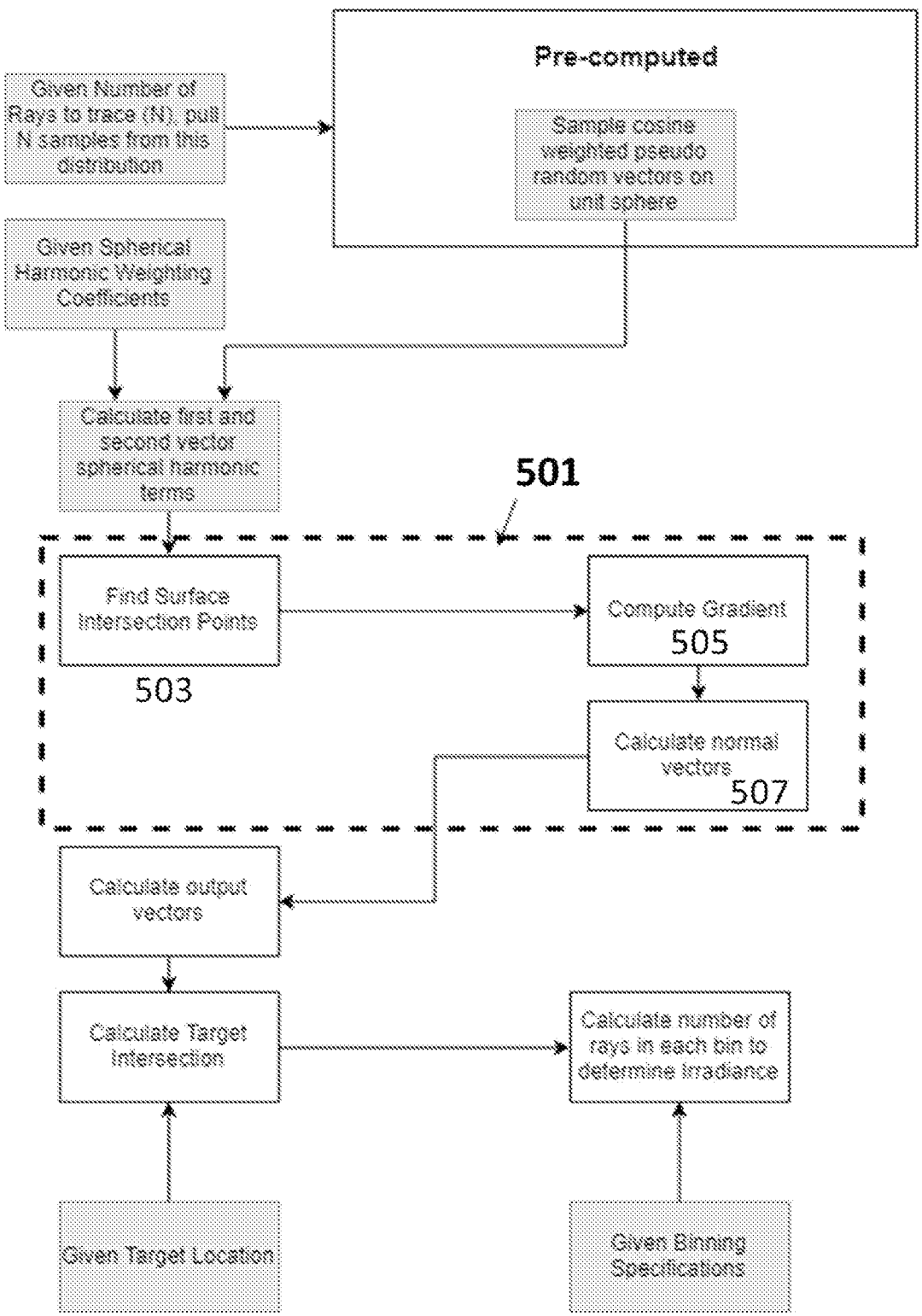
FIG. 5A is an example flowchart representation of an optical design process using polynomial functions in the Cartesian coordinates to represent a lens surface.

The disclosed techniques, among other features and benefits, improve the speed of ray tracing operations in various embodiments by representing an optical surface in an optical system based on the incoming vector field of light beams. FIG. 5A is a flowchart representation of a conventional optical design process in which polynomial functions in Cartesian coordinates are used to represent a lens surface. The process starts with a given number of rays to trace (e.g., N) that are provided to a precomputed sample cosine weighted pseudo random vectors on unit sphere based on N ray samples from a distribution. The first and second vector spherical harmonic terms are calculated based on a given set of spherical harmonic weighting coefficients. Block 501 includes some of the most computationally expensive steps of the design process: finding surface intersection points by stepping along a ray 501, computing surface gradients at the intersection points 503, and calculating normal vectors of the surface at the intersection points 505. The output vectors are then calculated based on the normal vectors, which are used to calculate target intersections based on the target locations. The number of rays in each bin is calculated based on a given binning specification to determine irradiance.

Figure 5B:
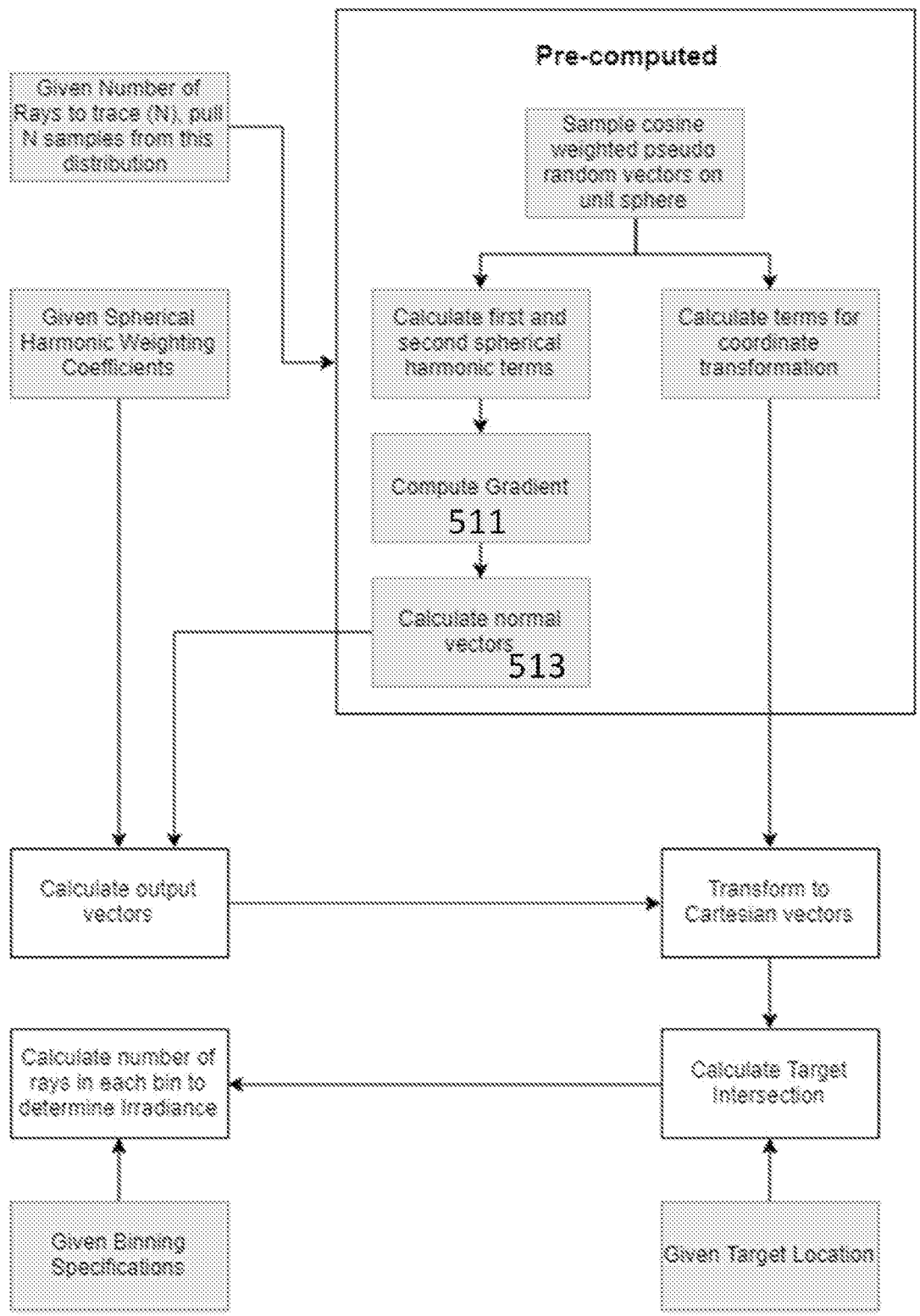
FIG. 5B is an example flowchart representation of an optical design process that characterizes a lens surface according to a vector field of the light source in accordance with the disclosed technology.

Using the disclosed techniques, the computationally expensive steps in block 501 can be entirely eliminated. As shown in FIG. 5B, because the surface is defined based on the vector field of the light, the intersection points can be obtained inherently for each vector (e.g., based on the radial distance from a light source). After the first and second spherical harmonic terms are calculated based on a given number of rays to trace and the spherical harmonic weighting coefficients, corresponding surface gradient 511 and normal vectors 513 can be pre-computed, thereby providing more efficient performance results given a set of design parameters. The output vectors can be calculated based on the given spherical harmonic weighting coefficients and the normal vectors computed at 513; the terms for coordinate transformation are also precomputed to allow transformation of the calculated output vectors into Cartesian vectors. The target intersections are calculated based on target locations, and are used to calculate the number rays in each bin, for a given binning specification, to determine irradiance.

Figure 6B:
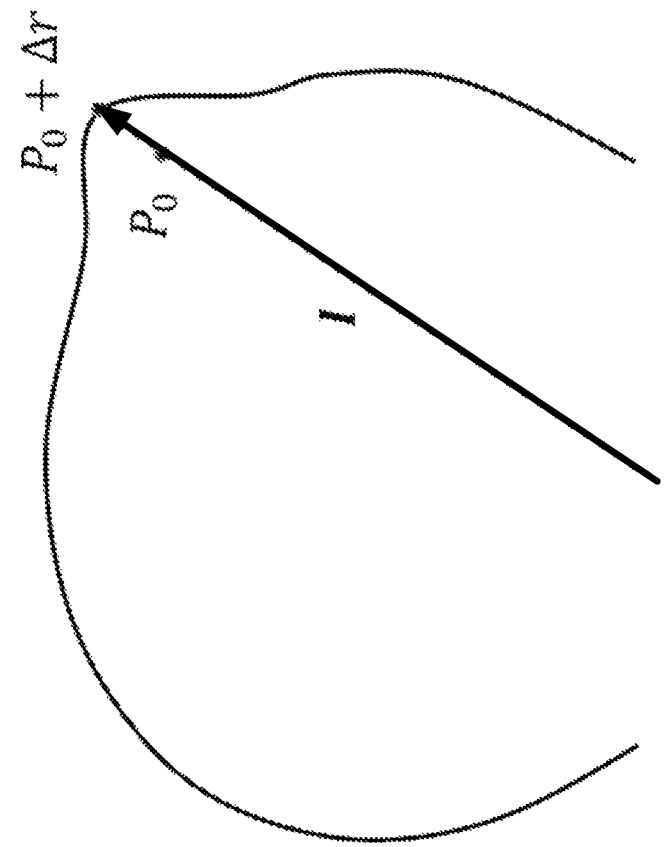
FIG. 6B illustrates an example of a surface change with respect to a vector field of a light source when the surface is represented by a coordinate system in accordance with the disclosed technology.
Figure 6A:
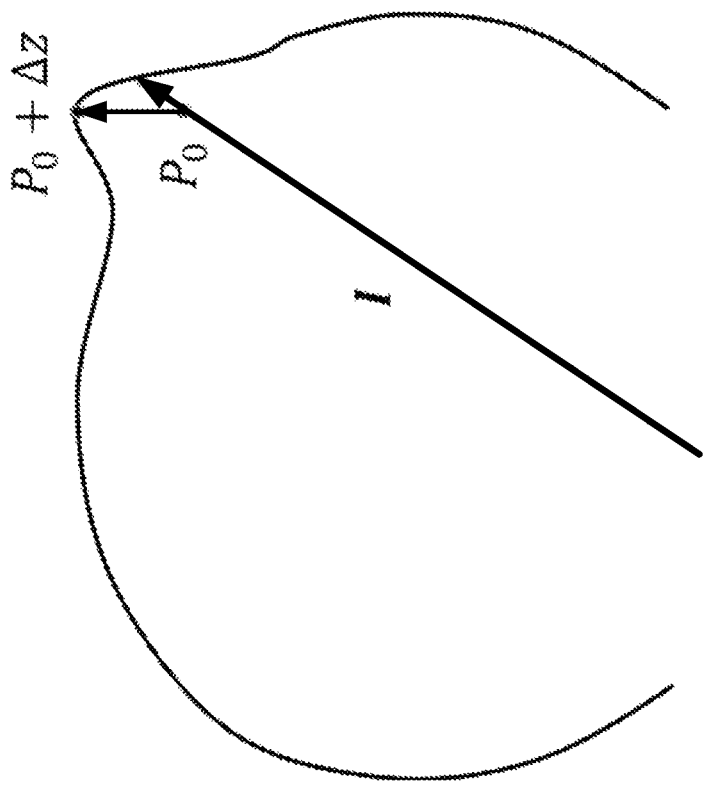
FIG. 6A illustrates an example of a surface change with respect to a vector field of a light source when the surface is represented in Cartesian coordinates.

Furthermore, because the surface is defined based on the incoming vector field of the light, surface changes will remain consistent with respect to the vector field, thereby simplifying iterative computation steps in the optimization part of the design process. FIG. 6A shows an example of a surface change with respect to a vector field of a light source when the surface is represented in Cartesian coordinates. In this example, a change in the surface that, for example, moves the point $P_0$ to $P_0 + \Delta z$, would cause the ray to deviate from the vector direction I, necessitating the same computation steps (e.g., determining intersection points, calculation surface gradient and normal) to be performed again for future iterations. When the surface is defined according to the vector field of the light, as shown in, for example, FIG. 6B, a surface change that causes the shift from $P_0$ to $P_0 + \Delta r$, would result in a change along the same direction as the vector I and thus can be represented in the same way as the original surface. Therefore, the corresponding intersection point, surface gradient, or surface normal can be readily determined without a need for complex operations.

Figure 6D:
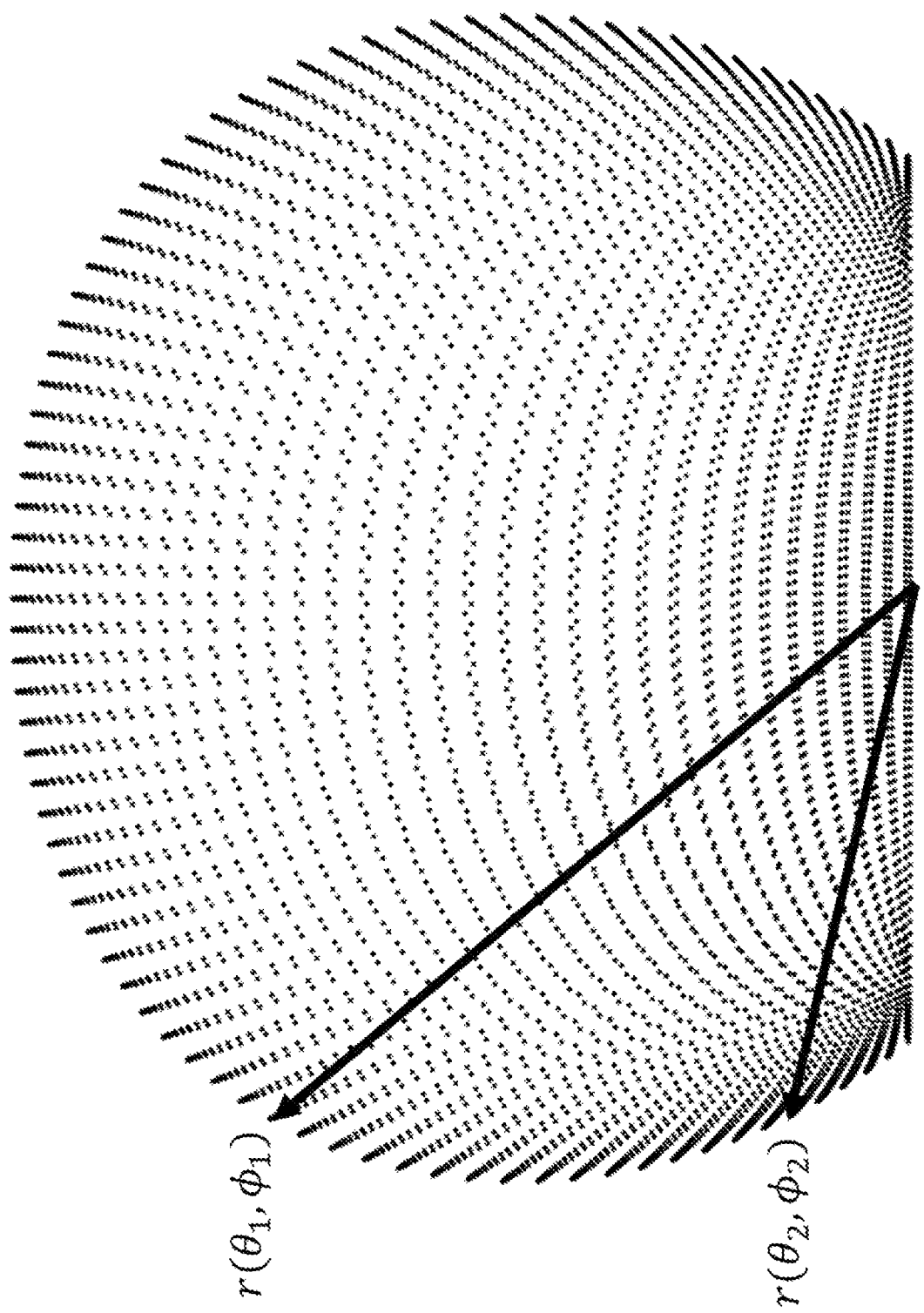
FIG. 6D illustrates an example of a one-to-one correspondence between a light vector and an intersection point in accordance with the disclosed technology.

Another potential issue with representations in Cartesian coordinates is that, in representing a point on the lens surface, a particular pair X-Y coordinates may correspond to multiple values along the Z axis, resulting in multiple points on the lens surface. FIG. 6C shows an example of a one-to-many correspondence using a polynomial representation in Cartesian coordinates. As shown in FIG. 6C, a given value along the X axis (x=a) can correspond to both $z_1$ and $z_2$ values along the Z axis. Thus, the representation for the lens surface cannot be simplified by using the X-Y coordinates only. The disclosed techniques can be used to eliminate this issue in various embodiments. For example, as shown in FIG. 6D, because the surface is defined using the vector field of the light, each vector of the light corresponds to exactly one intersection point on the surface.

Figure 7A:
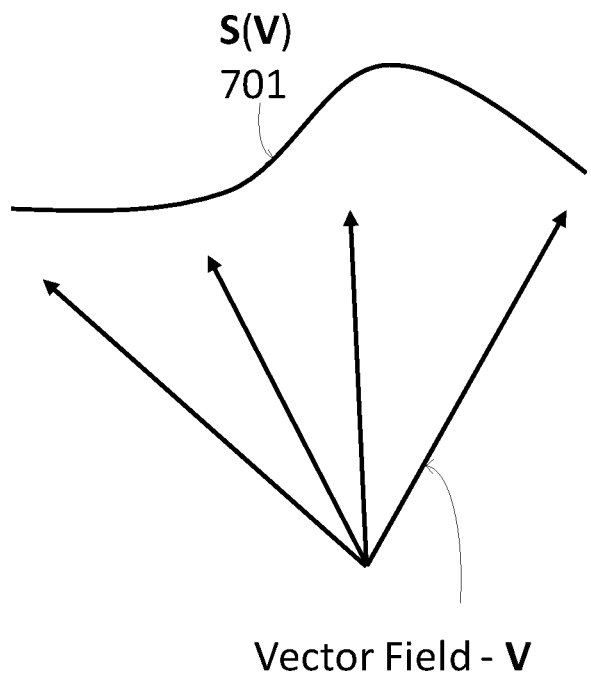
FIG. 7A illustrates an example of a surface characterized based on a vector field of light beams in accordance with the disclosed technology.
Figure 7B:
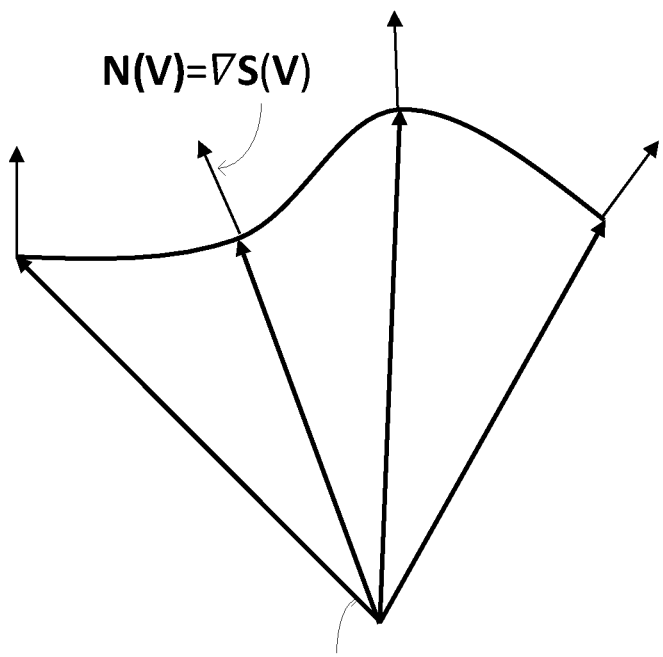
FIG. 7B illustrates an example of a determination of a surface normal based on the representation shown in FIG. 7A in accordance with the disclosed technology.
Figure 7C:
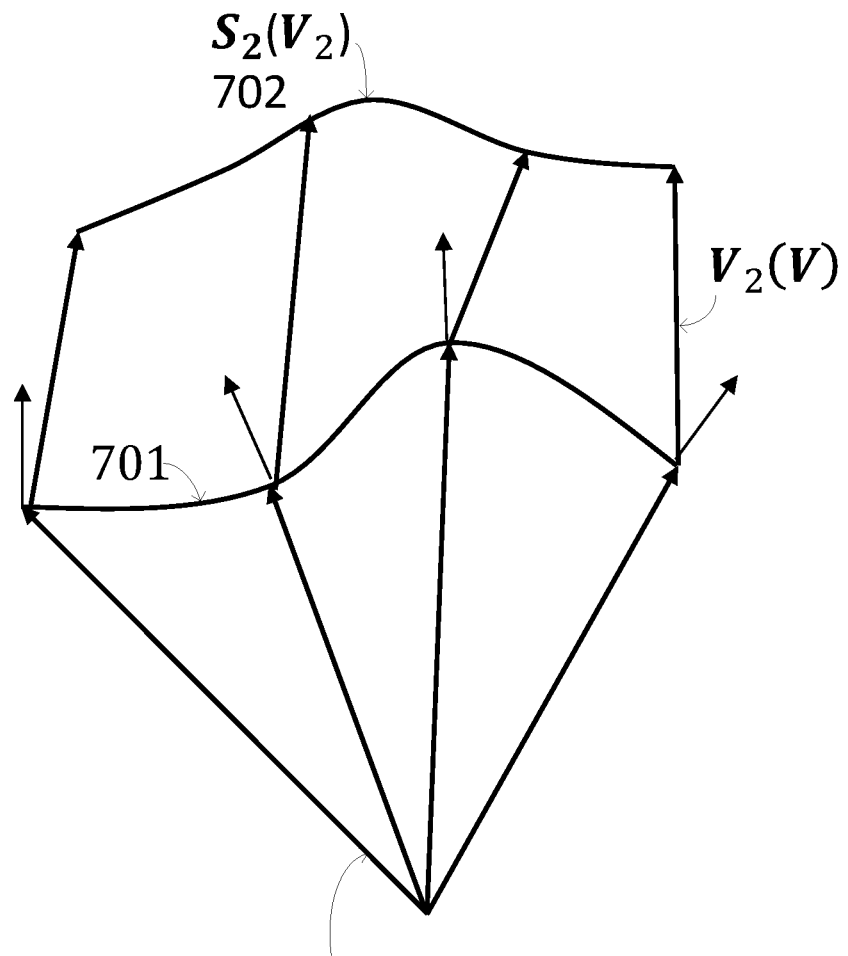
FIG. 7C is an example illustrating multiple surfaces represented according to a vector field of light beams in accordance with the disclosed technology.
Figure 7D:
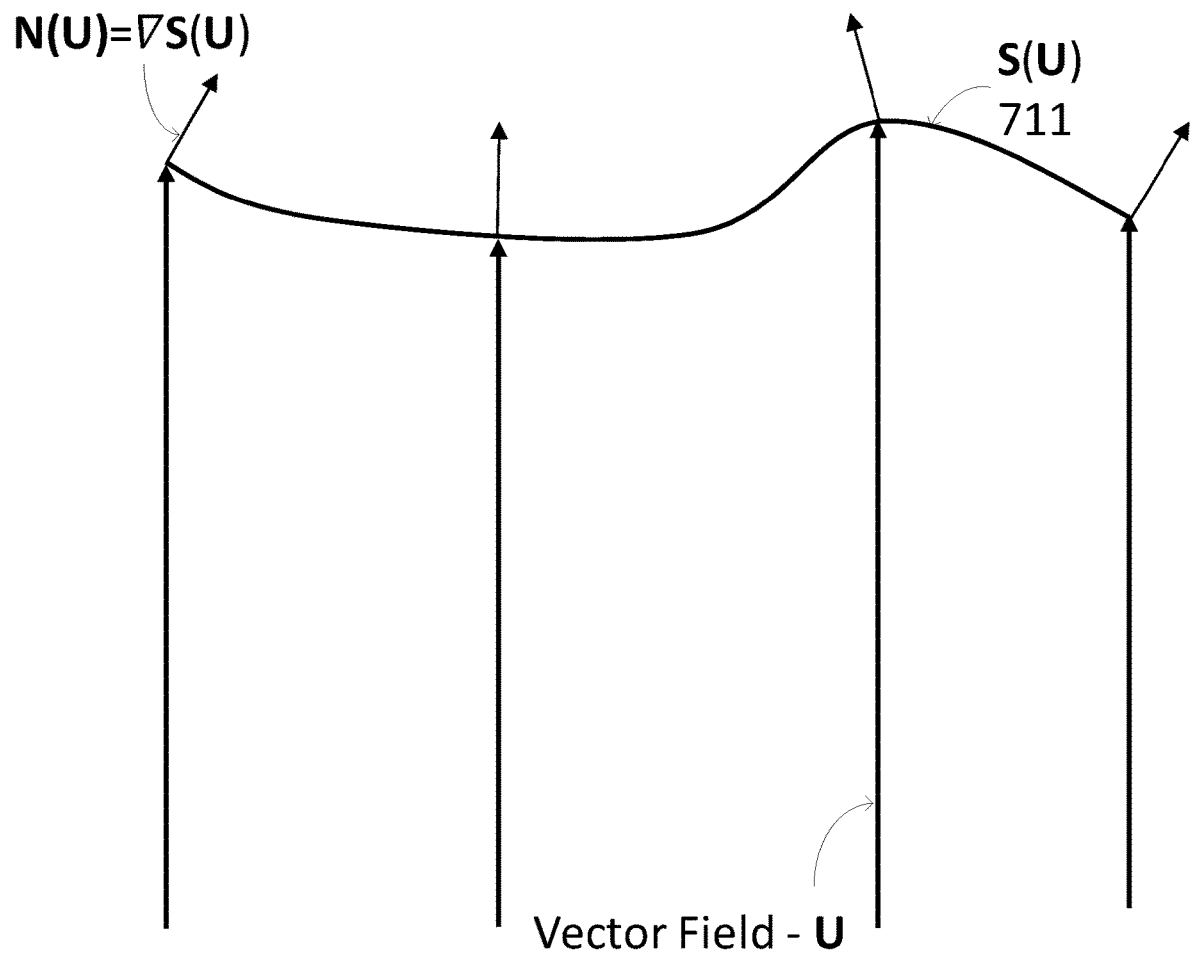
FIG. 7D illustrates another example of a surface represented according to a vector field of light beams in accordance with the disclosed technology.

FIG. 7A illustrates an example of a surface defined based on a vector field of light beams in accordance with the disclosed technology. In this example, the vector field of a point light source is denoted as V. The surface 701 is defined as S(V). FIG. 7B shows the corresponding normal calculation $N(V) = \nabla S(V)$. FIG. 7C is an example illustrating multiple surfaces represented according to a vector field of light beams in accordance with disclosed technology. The first surface 701 is represented according to the vector V. As the light rays intersect the first surface 701, they are refracted into different directions. The second vector field of refracted light rays can be represented based on the vector V as well: $V_2(V)$. Thus, additional surfaces can be defined according to the vector field. For example, a second surface 702 is represented as $S_2(V_2)$, where $V_2$ is a function of V. FIG. 7D is another example of a surface represented according to a vector field of a light source in accordance with the disclosed technology. In this example, the vector field of a set of collimated light rays is denoted as U. The surface 711 is identified as S(U), and the surface normal can be pre-calculated as $N(U) = \nabla S(U)$.

Figure 8:
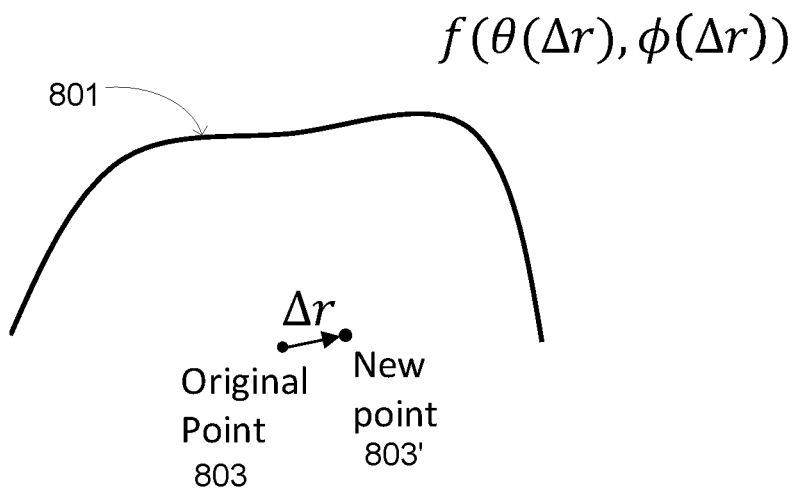
FIG. 8 illustrates an example of a surface representation in accordance with the disclosed technology when a light source has a translational displacement.
Figure 9:
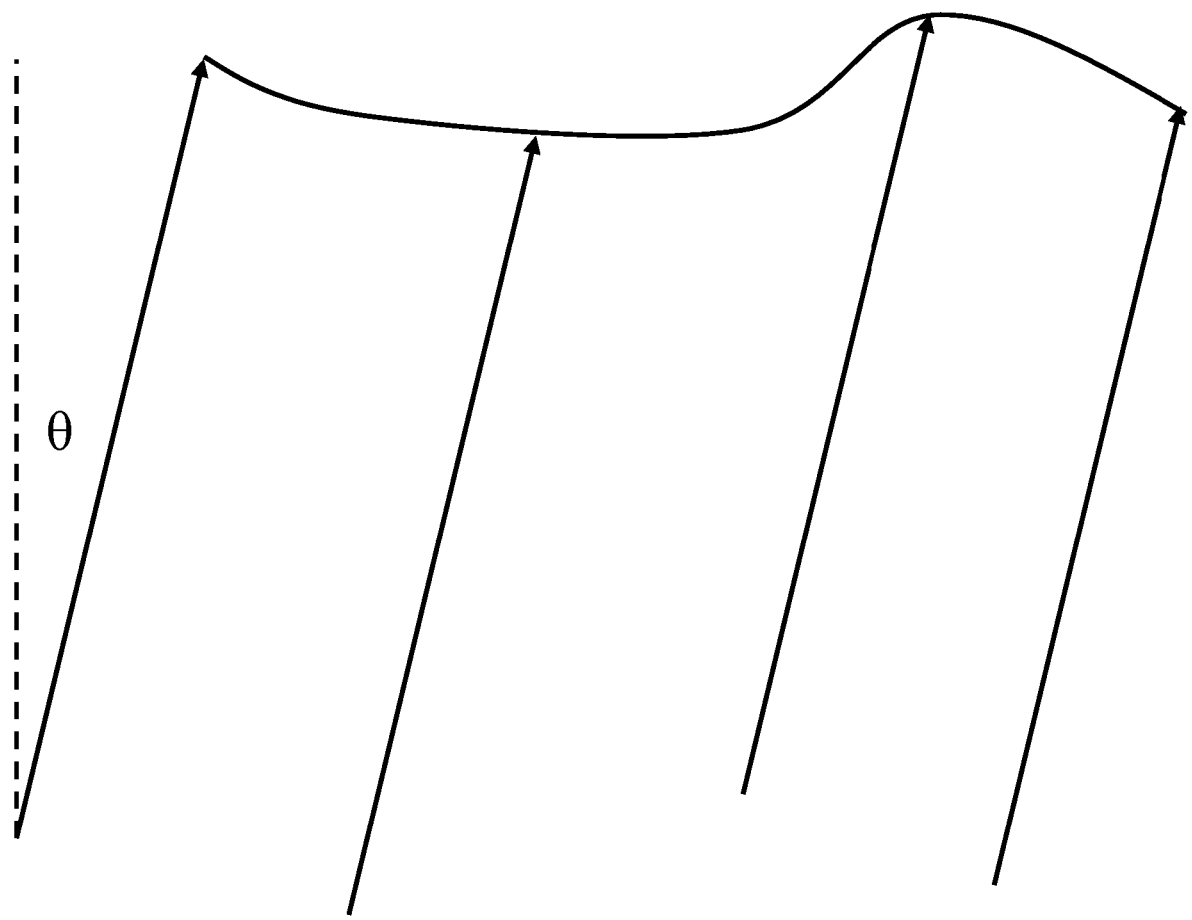
FIG. 9 illustrates an example of a surface representation in accordance with the disclosed technology when a light source has a rotational displacement.

In some embodiments, a translational or rotational displacement can be introduced to model an extended light source as a superposition of translated and/or rotated point sources or collimated sources. FIG. 8 shows an example of a surface representation in accordance with the disclosed technology when a light source has a translational displacement. The translational displacement can be represented in a similar way that corresponds to the vector field of the light. As shown in FIG. 8, the new light source 803' is placed within the lens 801 with a translational displacement of $\Delta r$ from the original light source position 803. The lens surface can be defined as $f(\theta(\Delta r), \phi(\Delta r))$. Similarly, FIG. 9 shows an example of a surface representation in accordance with the disclosed technology when a light source has a rotational displacement of degree θ. The lens surface can be re-defined after taking into account of the rotational component of the vector field.

In some embodiments, the vector field can be represented using spherical coordinates, and the lens surface can be represented using spherical harmonics. A specific set of spherical harmonics, denoted $Y_l^m(\theta, \phi)$, is called Laplace's spherical harmonics, where l represents the degree of the spherical harmonics. Various surfaces or functions can be expanded as a linear combination of the spherical harmonics. Higher degrees of spherical harmonics can be used to represent complex shapes. For example, in some embodiments, a 14-degree spherical harmonics representation can provide sufficient surface details for a desired lens.

Figure 10A:
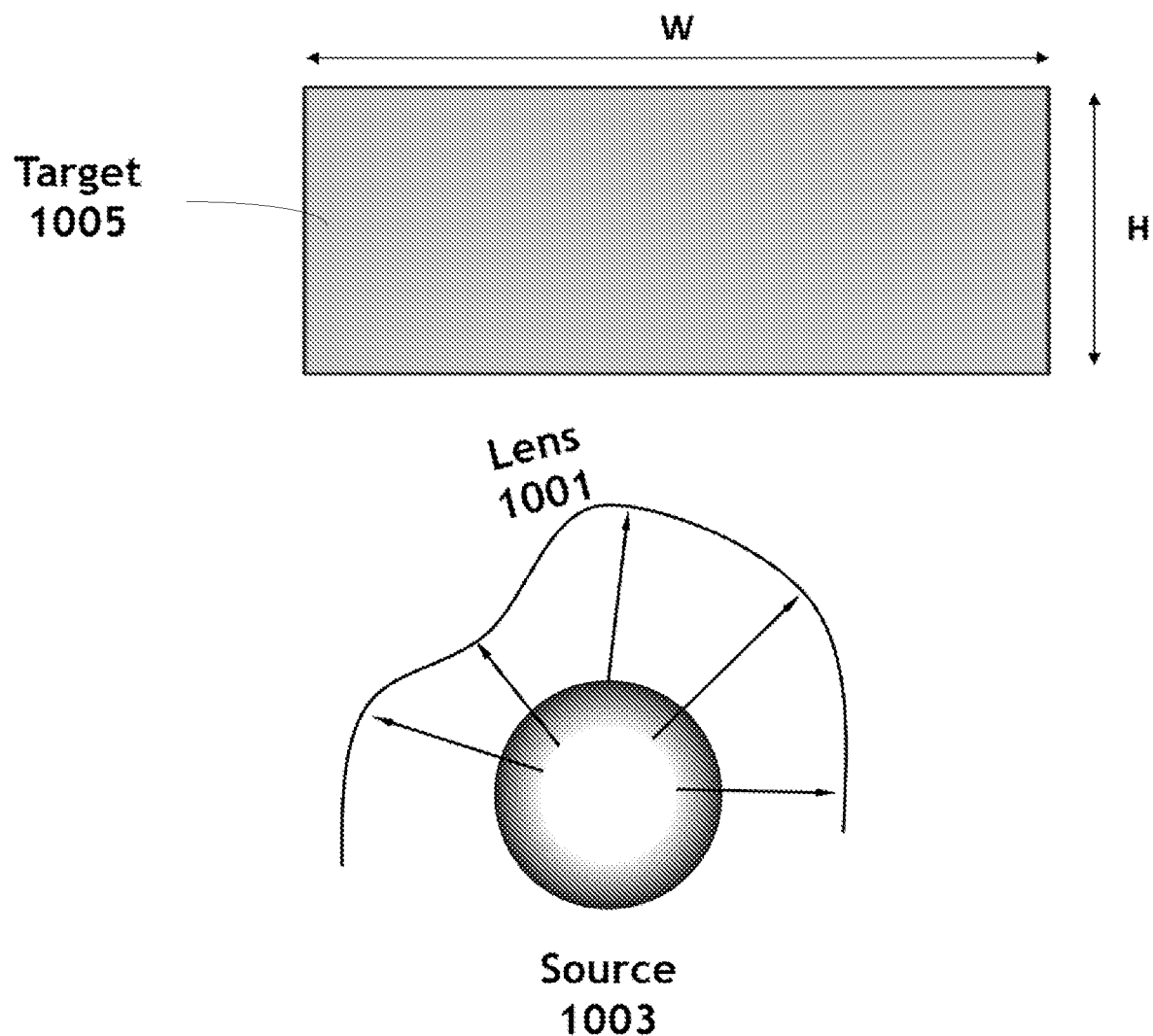
FIG. 10A illustrates an example of an optical design configuration in accordance with the disclosed technology.
Figure 10B:
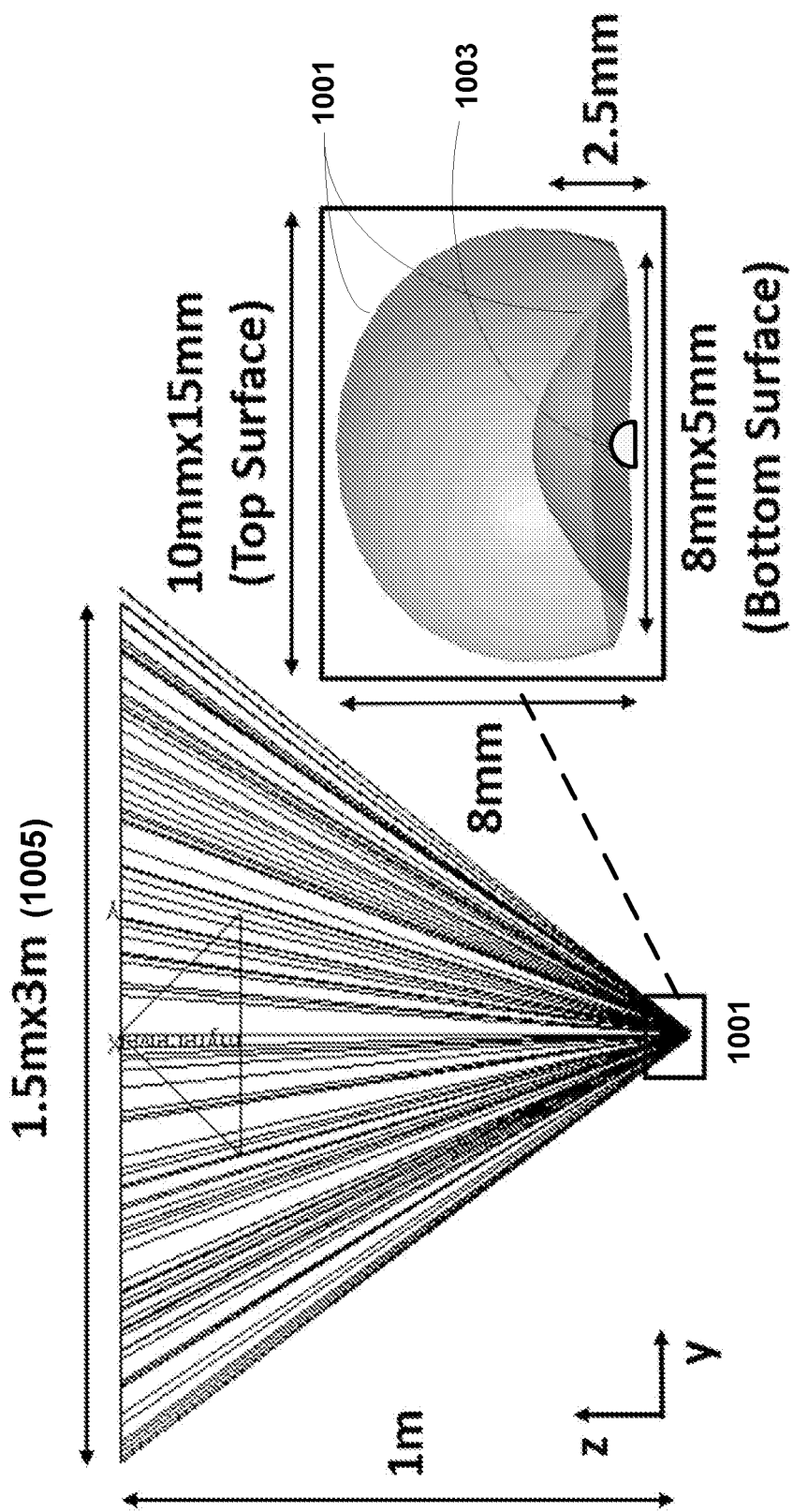
FIG. 10B illustrates additional details of the optical design configuration depicted in FIG. 10A in accordance with the disclosed technology.

FIG. 10A illustrates an example of an optical design configuration in accordance with the disclosed technology. In this example, the target area 1005 has a rectangular shape, with a width W and a height H. A lens 1001 is placed around a light source 1003. The goal of the design process is to determine the surface parameters of the lens 1001 so that the irradiance pattern can optimally match the target area 1005. FIG. 10B illustrates some of the additional details of the optical design configuration depicted in FIG. 10A. In this particular example, the light source 1003 includes a 1 mm by 1 mm Light Emitting Diode (LED). The example lens 1001 is a two-surface freeform refractive optical component that can be used to redirect a hemispherical emission of the 1 mm by 1 mm LED 1003 onto a 3 m by 1.5 m rectangular target area 1005 that is located 1 m away from the light source. The numbers that are shown in FIG. 10B around the rectangular area encompassing the light source 1003 and the lens 1001 provide example values of the dimensions of the lens that can be obtained through the design process. For example, to construct the lens surfaces, an iterative surface construction method is used. In this particular example, the method allocates 30% of the optical power to the bottom surface and 70% to the top surface. The 30%-70% allocation scheme can be used to maximize the compactness of the design, with the first surface being only 2.5 mm above the LED 1003 at the apex, and the second surface only 5.5 mm above the first surface.

In some embodiments, the optical surface of the component of interest can be represented using spherical components. To facilitate the understanding of the disclosed embodiments, the following section provides an overview of how representations using spherical harmonics can be leveraged to improve the optical design process.

For example, a lens surface can be described as a weighted summation of spherical harmonic terms:

$$f(\theta, \phi) = \Sigma_{l,m} F_{l,m} Y_l^m(\theta, \phi) \quad \text{Eq. (1)}$$

In Equation (1), $F_{l,m}$ terms are the weighting factors; these weighting factors are variables and take the form of a real-valued vector; i.e., one value for each combination of l, m. $Y_l^m(\theta, \phi)$ terms in Equation (1) are the standard spherical harmonics described as:

$$Y_l^m(\theta, \phi) = \sqrt{\frac{(2l+1)}{4\pi}\frac{(l-m)!}{(l+m)!}} P_l^m(\cos\theta)e^{im\phi}. \quad \text{Eq. (2)}$$

$P_l^m(\cos\theta)$ denotes the associated Legendre polynomials, where cos has been inserted for x. The generating formula is $$P_l^m(x) = \frac{(-1)^m}{2^l l!}(1-x^2)^{m/2}\frac{\partial^{l+m}}{\partial x^{l+m}}(x^2-1)^l. \quad \text{Eq. (3)}$$

The surface normal vector field of an implicit surface can be described as follows:

$$N = \nabla f(r, \theta, \phi) = f(\theta, \phi)(\hat{r} - \nabla f(\theta, \phi)) \quad \text{Eq. (4)}.$$

Writing the gradient explicitly yields $$f(\theta, \phi)\nabla f(\theta, \phi) = \sum_{l,m} F_{l,m}\left(\frac{\partial Y_l^m(\theta, \phi)}{\partial\theta}\hat{\theta} + im\frac{Y_l^m(\theta, \phi)}{\sin\theta}\hat{\phi}\right). \quad \text{Eq. (5)}$$

Thus, the complete function for the normal vectors can be expressed as:

$$N = \sum_{l,m} F_{l,m}\left(Y_l^m(\theta, \phi)\hat{\theta} - im\frac{Y_l^m(\theta, \phi)}{\sin\theta}\hat{\phi}\right). \quad \text{Eq. (6)}$$

The vector components can be grouped together so that the normal vectors are expressed as:

$$N = N_r\hat{r} + N_\theta\hat{\theta} + N_\phi\hat{\phi} \quad \text{Eq. (7)}.$$

When the light vector field is formed by a point source, it comprises entirely of radial components: $v_{in}=\hat{r}$. The refraction of the light beams can be calculated as follows.

Let's define a constant C, $$C = -n_1 N_r - \sqrt{1-n_1^2(1-N_r^2)} \quad \text{Eq. (8)}.$$

The outgoing vector field can be expressed as follows based on Snell's law:

$$v = n_1\hat{r} + CN \quad \text{Eq. (9)}.$$

The intersection locations with the target plane T can be determined by a change of coordinates into Cartesian coordinates:

$$\begin{bmatrix}\hat{x}\\\hat{y}\\\hat{z}\end{bmatrix} = \begin{bmatrix}\sin(\theta)\cos(\phi) & \cos(\theta)\cos(\phi) & -\sin(\phi)\\\sin(\theta)\sin(\phi) & \cos(\theta)\sin(\phi) & \cos(\phi)\\\cos(\theta) & -\sin(\theta) & 0\end{bmatrix}\begin{bmatrix}\hat{r}\\\hat{\theta}\\\hat{\phi}\end{bmatrix}, \quad \text{Eq. (10)}$$

$$v_x = \sin(\theta)\cos(\phi)v_r + \cos(\theta)\cos(\phi)v_\theta - \sin(\theta)v_\phi, \quad \text{Eq. (11)}$$

$$v_y = \sin(\theta)\cos(\phi)v_r + \cos(\theta)\sin(\phi)v_\theta + \cos(\theta)v_\phi, \quad \text{Eq. (12)}$$

$$v_z = \cos(\theta)v_r - \sin(\theta)v_\theta, \quad \text{Eq. (13)}$$

P is a vector containing the surface locations converted into cartesian coordinates, T is a two-vector containing the X and Y intersection points on the target surface. Using the simple equation of the intersection between a ray and a plane, where $T_0$ denotes an arbitrary point on the target surface (in this case x=y=0; leaving only the z location of the target $_{0,z}$) the target locations can be solved. $N_T$ denotes the target normal (which only has a z component in this example).

$$T = \left(\frac{(T_0 - P)\cdot N_R}{v\cdot N_T}\right)v + P, \quad \text{Eq. (14)}$$

$$N_T = \hat{z}, \quad \text{Eq. (15)}$$

$$T = \left(\frac{(T_{0,z} - P_z)}{v_z}\right)v + P, \quad \text{Eq. (16)}$$

$$T = \langle x_t(\theta, \phi), y_t(\theta, \phi)\rangle. \quad \text{Eq. (17)}$$

Figure 11A:
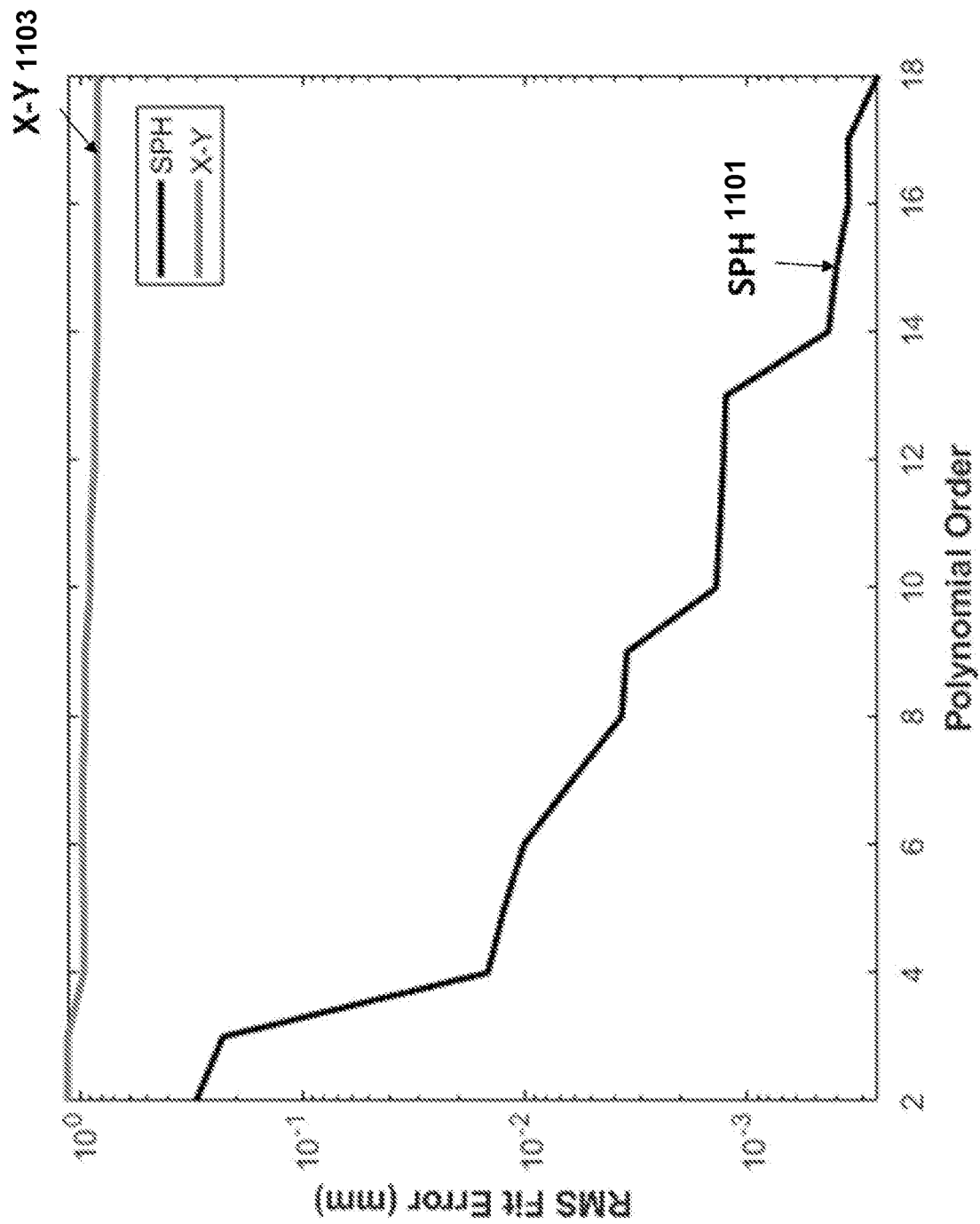
FIG. 11A illustrates a representative plot illustrating differences in root-mean-square (RMS) error between a X-Y polynomial representation and a spherical harmonics representation of a lens surface in accordance with the disclosed technology.

As verified through empirical data, the disclosed techniques can provide significant performance benefits for the optical design process. FIG. 11A is a representative plot showing a comparison in root-mean-square (RMS) error between a X-Y polynomial representation and a spherical harmonics representation of a lens surface. The spherical harmonics performance 1101 improves as the polynomial order increases while the X-Y polynomial representation 1103 fails to improve much at all no matter how large the polynomial becomes.

As another example, in one embodiment, 250,000 rays emitted from a point source were traced through a single-surface freeform lens. A single raytracing step using the highest precision on a single Central Processing Unit (CPU) core takes 20 seconds to complete with commercial software programs, such as LightTools. By changing the surface representation based on the vector field of the point light source, the same raytracing step only takes 0.026 seconds using a compiled Matlab executable file (250,000 rays using a single CPU core), demonstrating a ~800× performance gain.

Figure 11B:
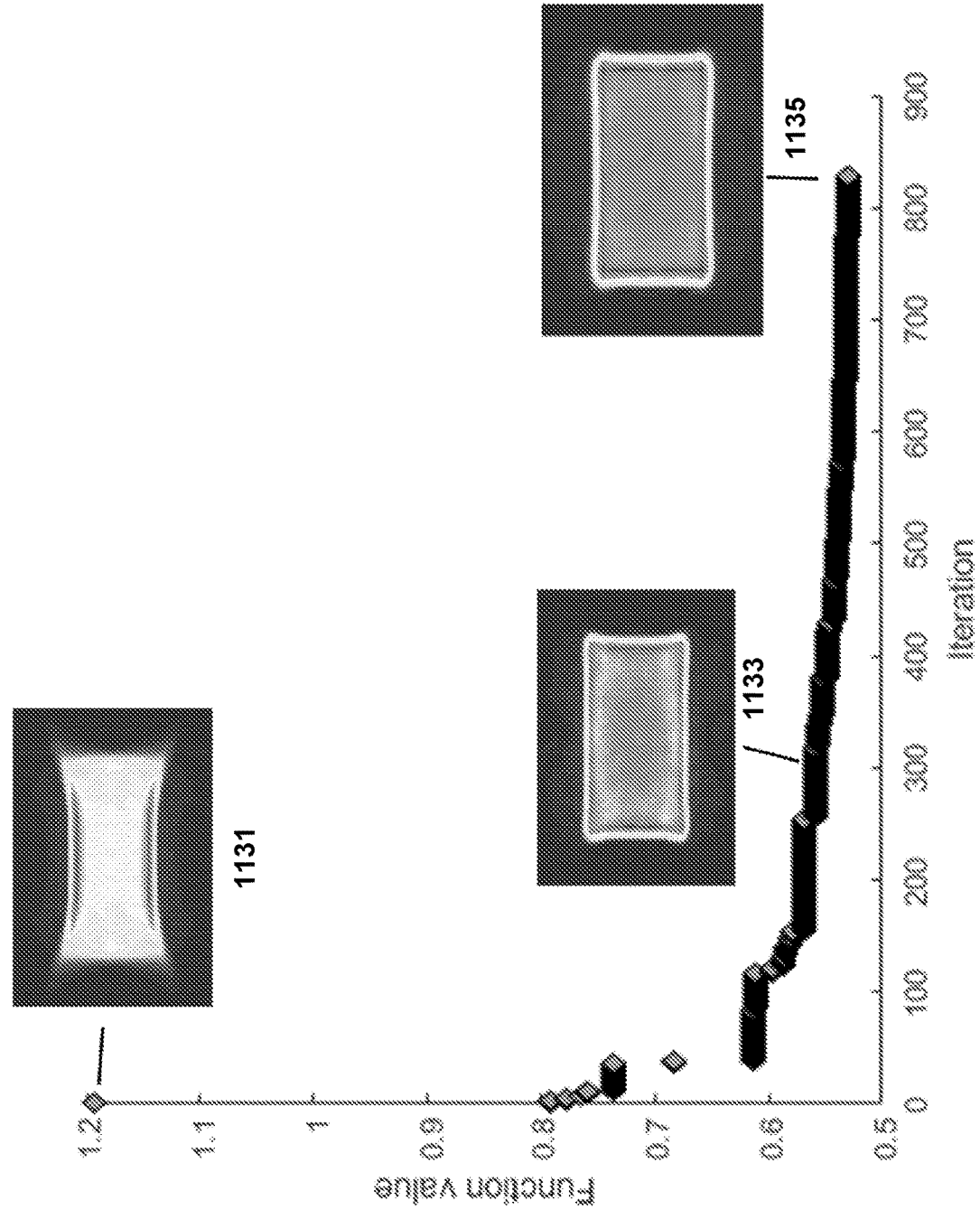
FIG. 11B illustrates another representative plot illustrating performance differences as the number of iterations increases in an optimization process in accordance with the disclosed technology.

FIG. 11B is another example plot showing performance differences as the number of iterations increases in the optimization part of the optical design process. In this example, each iteration along the optimization process requires tracing 125,000 rays, modifying the surface shape, and recalculating the surface normal. The horizontal axis shows the number of iterations for the optimization. The vertical axis indicates a performance function value of the resulting optical design that corresponds to an irradiance pattern. It is noted that the irradiance patterns shown in this example include a black border that is not a part of the illuminated area. In each of the irradiance patterns, the lighter gray shades in the target area (e.g., the initial target area 1131 at iteration 0) indicate that the target area was poorly illuminated. The irradiance pattern improves rapidly as the iterations progresses, as indicated by the darker shades of gray in the target area such as 1133, 1135. More than 800 iterations were completed in less than 6 seconds in an embodiment using the disclosed techniques. In comparison, commercial software programs such as LightTool take around 2.22 hours on high precision settings with a single CPU core to complete the same computation.

Figure 12A:
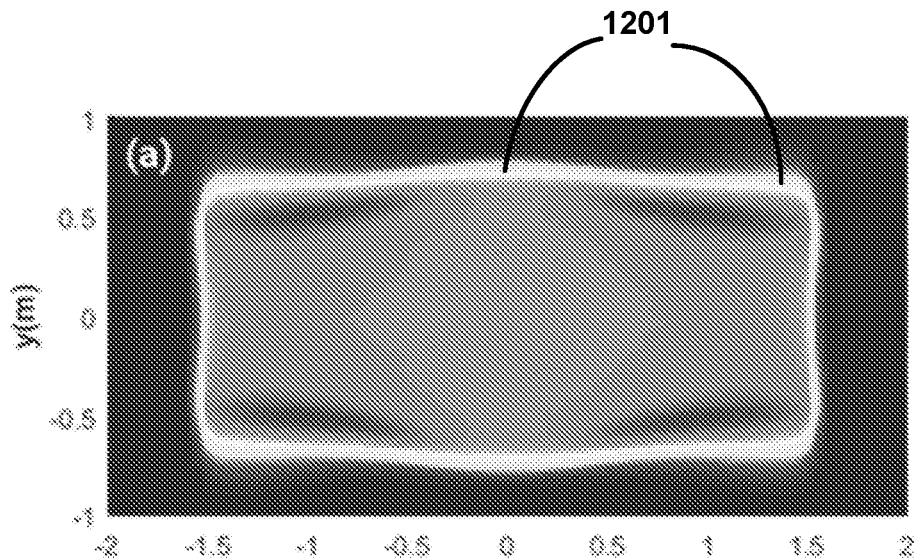
FIG. 12A illustrates an example of an irradiance pattern generated by the lens with an example Light Emitting Diode (LED) emitting into a full hemisphere before optimization in accordance with the disclosed technology.
Figure 12B:
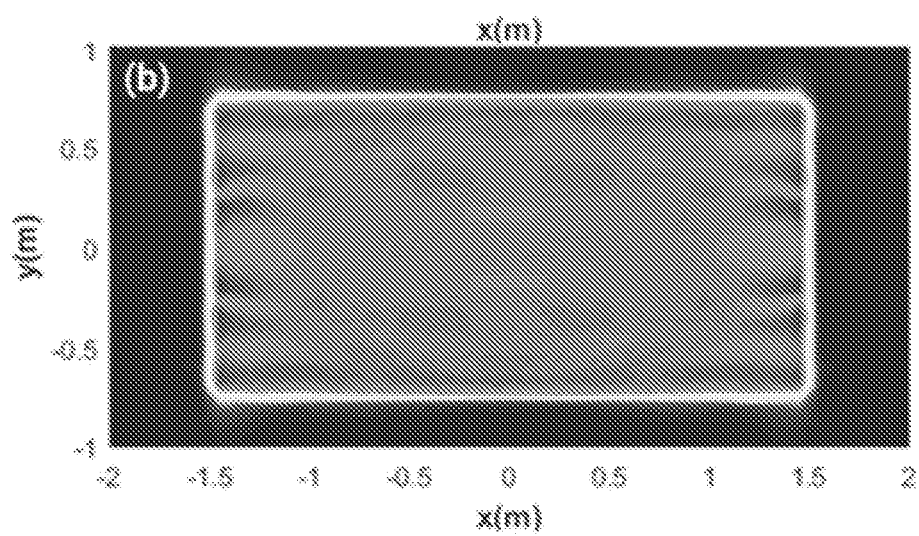
FIG. 12B illustrates an example of an irradiance pattern generated by the lens with an LED emitting into a full hemisphere after optimization in accordance with the disclosed technology.

FIGS. 12A and 12B illustrate examples of irradiance patterns generated by a 1 mm by 1 mm LED source emitting into a full hemisphere and surrounded by the lens before and after optimization, respectively. The dark border around the target area in each irradiance pattern shows that that the border area is not illuminated. As shown in FIG. 12A, before optimization the initial irradiance pattern includes a curvature 1201 along the edges of the target area. The optimized irradiance pattern using the disclosed techniques as shown in FIG. 12B is much closer to the desired effect for the target area.

Figure 13A:
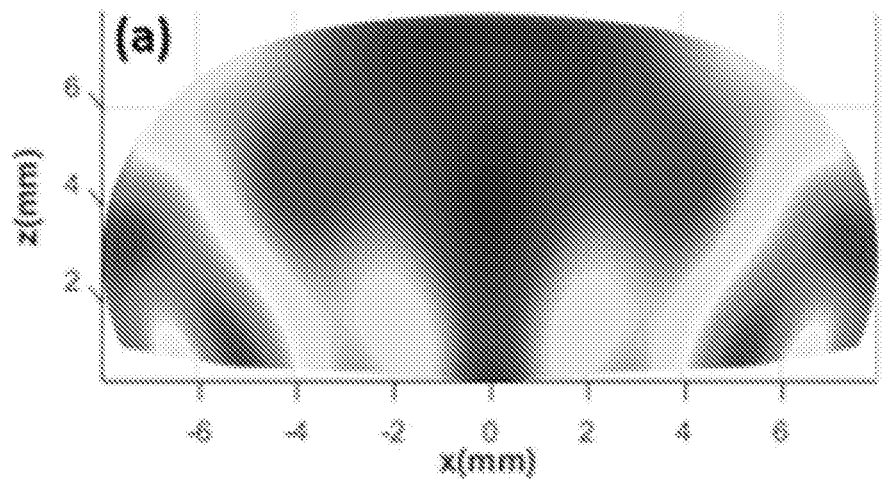
FIG. 13A illustrates a side profile of the top surface shown in FIG. 10B after optimization steps in accordance with disclosed technology.
Figure 13B:
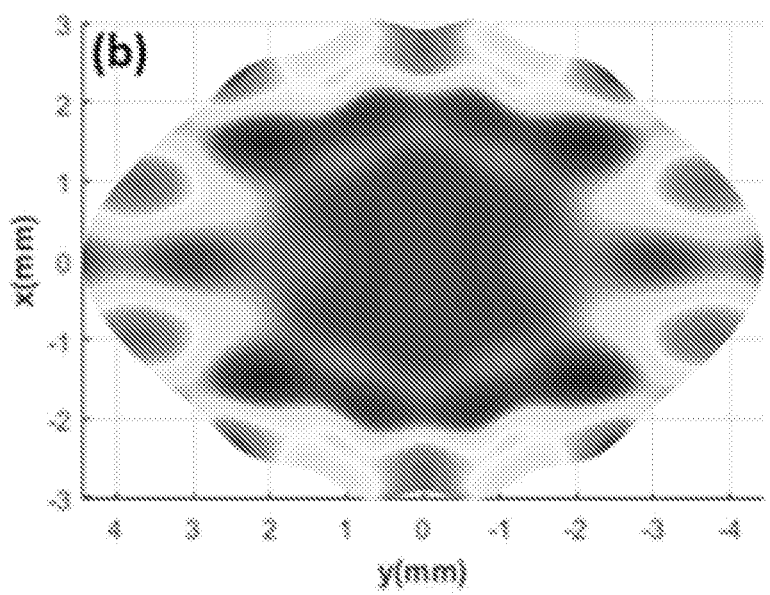
FIG. 13B illustrates a top-down view of the bottom surface shown in FIG. 10B after optimization steps in accordance with the disclosed technology.

FIG. 13A shows a side profile of the top surface shown in FIG. 10B after optimization steps in accordance with disclosed technology. FIG. 13B shows a top-down view of the bottom surface shown in FIG. 10B after optimization steps in accordance with disclosed technology. Using the disclosed techniques in various embodiments, irregular adjustments can be introduced to each surface based on the vector field of the LED light source without impacting computational accuracy or time.

Figure 14A:
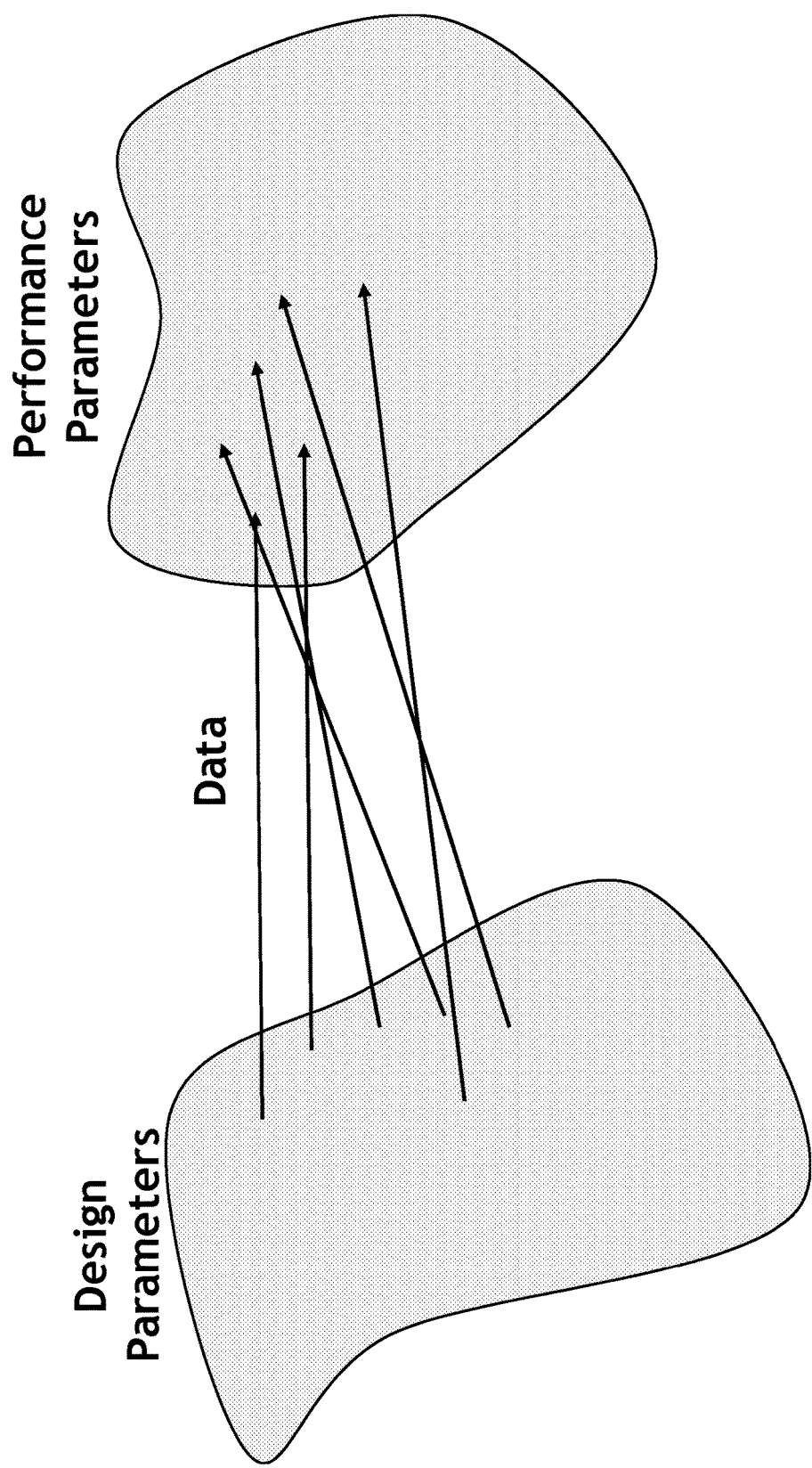
FIG. 14A illustrates a schematic diagram of a space of design parameters that maps to a space of performance parameters.
Figure 14B:
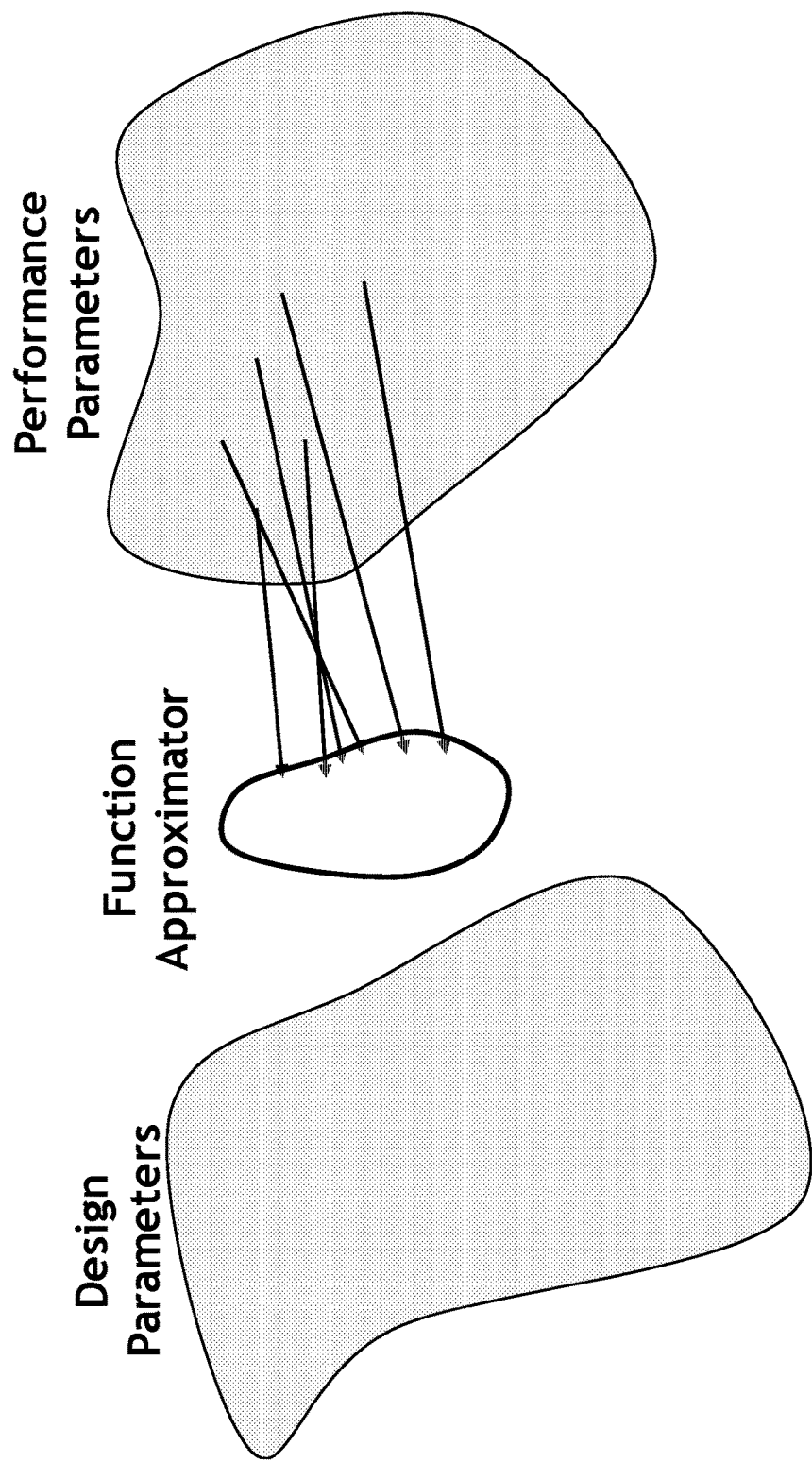
FIG. 14B illustrates an example of a functional approximator that can facilitate an estimation of design parameters based on performance parameters in accordance with the disclosed technology.

The example described in connection with FIGS. 10A-13B demonstrates how design parameters map to performance parameters in the optical design process. This mapping is schematically shown in FIG. 14A. The example described above also demonstrates that the design process includes not only the mapping of the design parameters to the performance parameters, but also the inverse problem of determining proper design parameters based on a particular set of performance parameters. FIG. 14B is an illustration of an example function approximator that can facilitate estimation of the design parameters based on performance parameters. The function approximator can be trained using existing design parameters and performance parameters to derive optimal design parameters given a particular set of performance parameters. For example, as shown in FIG. 14C, given the function approximator and a particular set of performance parameters 1401, the corresponding design parameters can be determined.

Figure 15:
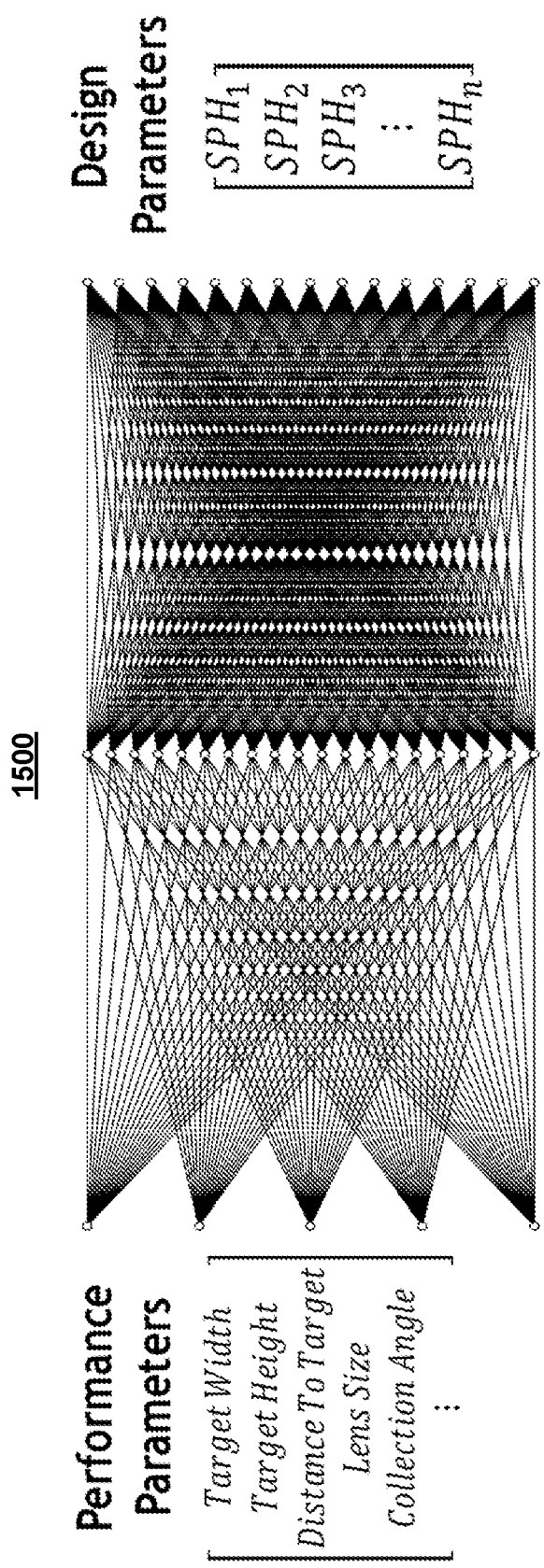
FIG. 15 illustrates an example of an artificial neural network that can be trained to produce desired design parameters in spherical harmonic coefficients based on performance parameters in accordance with the disclosed technology.

In some embodiments, the function approximator can be implemented using optimization algorithms such as gradient descent. In some embodiments, leveraging the high computational efficiency of the disclosed technology, an artificial neural network can be used to generate a continuous or semi-continuous mapping between the performance parameters and the design parameters. FIG. 15 shows an example of an artificial neural network 1500 that can be trained to produce desired design parameters in spherical harmonic coefficients based on performance parameters, such as target width, target height, distance to target area, lens size, etc.

FIG. 16A shows an example database of irradiance patterns produced by a neural network in accordance with disclosed technology prior to a training step. The database is represented by a two-dimensional grid. The horizontal axis of the grid represents the width of the target area (e.g., between 1500 mm to 4000 mm). The vertical axis of the grid represents the height of the target area (e.g., between 1500 mm to 4000 mm). The percentage error as compared to the ideal irradiance pattern in this example ranges from 4% to 12%. Each square in the grid represents an irradiance pattern corresponding to a set of design parameter for the corresponding target area. For example, the irradiance pattern 1631 of the lower-right square (e.g., representing a target area with width of 4000 mm and height of 1500 mm) has a high percentage error (e.g., ~12%). The lighter color in the irradiance pattern 1631 indicates that the target area is poorly illuminated. FIG. 16B shows an example database of irradiance patterns produced by the neural network in accordance with disclosed technology after a training step. The percentage error for the same square improves from ~12% to ~9%. The darker color in the irradiance pattern 1651 indicates that the target area is now better illuminated and demonstrates substantial improvement for the same target area after a single training step 1601. The neural network can be trained over time to obtain an accurate mapping of the parameters to assist the optical design process.

FIG. 17A shows an example of a manually-generated database that includes optimal mappings between performance parameters to design parameters. Similar to FIG. 16A, the database is represented by a two-dimensional grid. The horizontal axis of the grid represents the width of the target area (e.g., between 1500 mm to 4000 mm). The vertical axis of the grid represents the height of the target area (e.g., between 1500 mm to 4000 mm).

Each square in the grid represents an irradiance pattern corresponding to a set of design parameter for the corresponding target area. FIG. 17B shows an example database of irradiance patterns automatically generated by a trained neural network that maps between performance parameters to design parameters. FIG. 17C shows a difference between the databases shown in FIGS. 17A-17B. As shown in FIG. 17C, the differences between the two databases range between −0.14% to 0.6%. This demonstrate that the neural network trained using the disclosed techniques can be an accurate and efficient aid in assisting optical designs.

Figure 18:
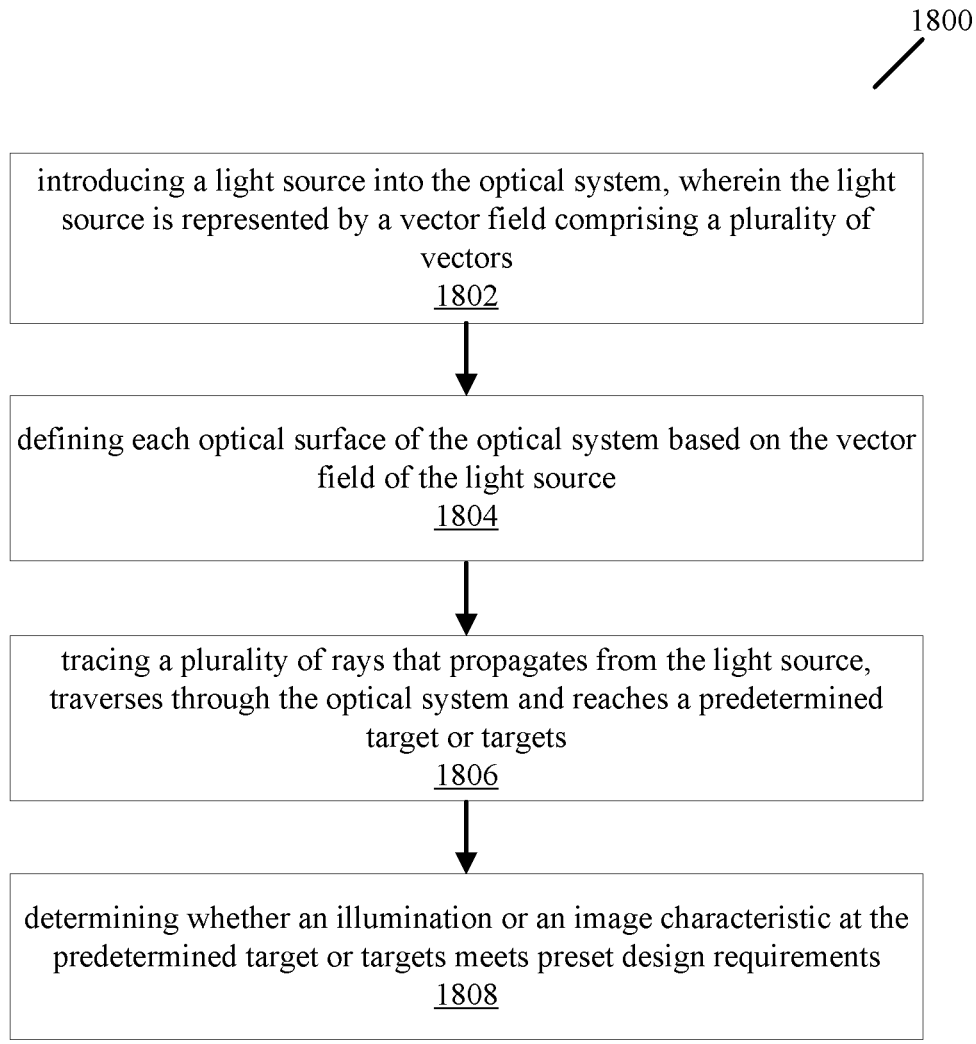
FIG. 18 illustrates a flowchart representation of a method for optical design in accordance with the disclosed technology.

FIG. 18 is a flowchart representation of an example method 1800 for optical design. The method 1800 includes, at 1802, introducing a light source into the optical system. The light source emits illumination that is characterized as a point source, a collimated illumination, or a superposition of one or more point sources or one or more collimated illuminations. The light source is represented by a vector field comprising a plurality of vectors. The method 1800 includes, at 1804, characterizing each optical surface of the optical system based on the vector field of the light source. The method includes, at 1806, tracing a plurality of rays that propagate from the light source, traverse through the optical system and reach a predetermined target or targets. Each of the plurality of rays are represented based on the vector field of the light source upon reflection, refraction, or transmission through or from each optical surface of the optical system. The method 1800 also includes, at 1808, determining whether an illumination or an image characteristic at the predetermined target or targets meets preset design requirements. The target may be a planar or a non-planar surface. In some embodiments, the target may be described by a desired angular distribution of light or an intensity profile.

FIG. 19 is another flowchart representation of an example method 1900 for optical design. The method 1900 includes, at 1902, positioning a light source within a lens. The light source is configured to emit multiple light beams that project through a surface of the lens to reach a target area. The light beams are characterized by a vector field comprising a plurality of vectors. The method 1900 includes, at 1904, iteratively performing an optimization procedure upon determining that an irradiance pattern formed by the light beams through the lens fails to meet one or more predetermined criteria for the target area. The optimization procedure includes adjusting a characteristic of one or more surfaces of the lens. Each of the one or more surfaces of the lens is represented based on the vector field of the light source. The optimization procedure includes determining, for each ray, intersection points between the one or more surfaces of the lens and the corresponding ray based on the vector field, and computing, for each ray, surface normal vectors corresponding to the intersection points. The surface normal vectors are represented based on the vector field of the light source. The optimization procedure also includes computing, for each ray, a trajectory of a refracted ray that exits the one or more surfaces based on the normal vectors, and updating the irradiance pattern using the refracted rays.

It is thus evident that the disclosed embodiments provide significant improvements over the existing systems by using the incoming vector field of the light source to define the surfaces, determine normal vectors and gradients, and enable tracing of the rays through the system based on the vector field of the light source. In the example of a point source, spherical harmonics is one example of a suitable representation of the vector field due to the spherical geometry. It should be noted, however, that the disclosed embodiments that use spherical harmonics do not map the spherical harmonics to a circular domain. Such mapping to a circular domain removes the capability of providing a vector field that is based on the light source, and would suffer from similar disadvantages that are associated with using Zernike and X-Y basis functions.

Figure 20:
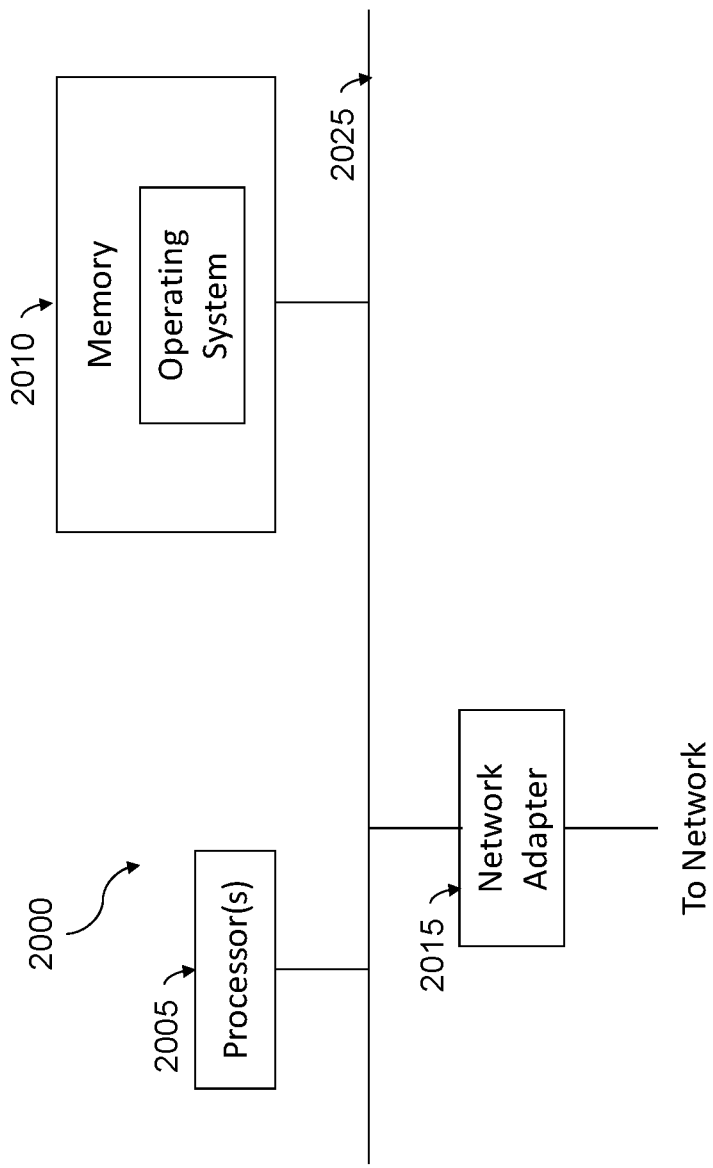
FIG. 20 illustrates a block diagram of an example computer system architecture or other control device that can be utilized to implement various portions of the presently disclosed technology.

FIG. 20 is a block diagram illustrating an example of the architecture for a computer system or other control device 2000 that can be utilized to implement various portions of the presently disclosed technology. In FIG. 20, the computer system 2000 includes one or more processors 2005 and memory 2010 connected via an interconnect 2025.

The interconnect 2025 may represent any one or more separate physical buses, point to point connections, or both, connected by appropriate bridges, adapters, or controllers. The interconnect 2025, therefore, may include, for example, a system bus, a Peripheral Component Interconnect (PCI) bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 674 bus, sometimes referred to as "Firewire."

The processor(s) 2005 may include central processing units (CPUs), graphics processing units (GPUs), or other types of processing units (such as tensor processing units) to control the overall operation of, for example, the host computer. In certain embodiments, the processor(s) 2005 accomplish this by executing software or firmware stored in memory 2010. The processor(s) 2005 may be, or may include, one or more programmable general-purpose or special-purpose microprocessors, digital signal processors (DSPs), programmable controllers, application specific integrated circuits (ASICs), programmable logic devices (PLDs), or the like, or a combination of such devices.

The memory 2010 can be or include the main memory of the computer system. The memory 2010 represents any suitable form of random access memory (RAM), read-only memory (ROM), flash memory, or the like, or a combination of such devices. In use, the memory 2010 may contain, among other things, a set of machine instructions which, when executed by processor 2005, causes the processor 2005 to perform operations to implement embodiments of the presently disclosed technology.

Also connected to the processor(s) 2005 through the interconnect 2025 is a (optional) network adapter 2015. The network adapter 2015 provides the computer system 2000 with the ability to communicate with remote devices, such as the storage clients, and/or other storage servers, and may be, for example, an Ethernet adapter or Fiber Channel adapter.

The processing devices that are described in connection with the disclosed embodiments can be implemented as hardware, software, or combinations thereof. For example, a hardware implementation can include discrete analog and/or digital components that are, for example, integrated as part of a printed circuit board. Alternatively, or additionally, the disclosed components or modules can be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application.

Various embodiments described herein are described in the general context of methods or processes, which may at least in-part be implemented by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, systems, and computer program products.

What is claimed is:

1. A method for designing an optical system including a light source and a plurality of optical surfaces, the method comprising:
    representing, by a computer processor, a light source in the optical system by a vector field comprising a plurality of vectors, wherein the light source is modeled to emit illumination that is characterized as a point source, a collimated illumination, or a combination of one or more point sources or one or more collimated illuminations;
    defining, by the computer processor, each optical surface of the optical system as a function of the vector field of the light source, wherein a surface normal of each optical surface is represented based on radial components of the vector field of the light source using spherical harmonics;
    tracing, by the computer processor, a plurality of rays that propagates from the light source, traverses through the optical system and reaches a predetermined target area, wherein each of the plurality of rays is represented based on the vector field of the light source upon reflection, refraction, or transmission through or from each optical surface of the optical system; and
    determining, by the computer processor, whether an illumination or an image characteristic at the predetermined target area meets one or more preset design requirements.

2. The method of claim 1, wherein tracing the plurality of rays includes determining an intersection point between at least one of the rays that is traced through the optical system and at least one of the plurality of optical surfaces, wherein the intersection point is determined based on the vector field of the light source.

3. The method of claim 1, wherein tracing the plurality of rays includes determining a normal vector to at least one of the plurality of optical surfaces, wherein the normal vector is also represented based on the vector field of the light source.

4. A method for designing an optical system including a light source and a plurality of optical surfaces, the method comprising:
    representing, by a computer processor, a light source in the optical system by a vector field comprising a plurality of vectors, wherein the light source is modeled to emit illumination that is characterized as a combination of one or more point sources or one or more collimated illuminations;
    determining the combination of the one or more point sources or one or more collimated illuminations by introducing a translational or rotational displacement based on the vector field of the light source;
    defining, by the computer processor, each optical surface of the optical system based on the vector field of the light source;
    tracing, by the computer processor, a plurality of rays that propagates from the light source, traverses through the optical system and reaches a predetermined target area, wherein each of the plurality of rays is represented based on the vector field of the light source upon reflection, refraction, or transmission through or from each optical surface of the optical system; and
    determining, by the computer processor, whether an illumination or an image characteristic at the predetermined target area meets one or more preset design requirements.

5. The method of claim 4, wherein one or more of the optical surfaces are represented using spherical harmonics.

6. An apparatus for optical system design, comprising:
    one or more processors; and
    a memory including processor-executable instructions stored thereon, the processor-executable instructions upon execution by the one or more processors configures the device to carry out a method that comprises:
    representing a light source in the optical system by a vector field comprising a plurality of vectors, wherein the light source is modeled to emit illumination that is characterized as a point source, a collimated illumination, or a combination of one or more point sources or one or more collimated illuminations;
    defining each optical surface of the optical system as a function of the vector field of the light source, wherein a surface normal of each optical surface is represented based on radial components of the vector field using spherical harmonics;
    tracing a plurality of rays that propagates from the light source, traverses through the optical system and reaches a predetermined target area, wherein each of the plurality of rays is represented based on the vector field of the light source upon reflection, refraction, or transmission through or from each optical surface of the optical system; and
    determining whether an illumination or an image characteristic at the predetermined target area meets one or more preset design requirements.

7. The apparatus of claim 6, wherein tracing the plurality of rays includes determining an intersection point between at least one of the rays that is traced through the optical system and at least one of the plurality of optical surfaces, wherein the intersection point is determined based on the vector field of the light source.

8. The apparatus of claim 6, wherein tracing the plurality of rays includes determining a normal vector to at least one of the plurality of optical surfaces, wherein the normal vector is also represented based on the vector field of the light source.

9. An apparatus for optical system design, comprising:
one or more processors; and
a memory including processor-executable instructions stored thereon, the processor-executable instructions upon execution by the one or more processors configures the device to carry out a method that comprises:
representing a light source in the optical system by a vector field comprising a plurality of vectors, wherein the light source is modeled to emit illumination that is characterized as a combination of one or more point sources or one or more collimated illuminations;
determining the combination of the one or more point sources or one or more collimated illuminations by introducing a translational or rotational displacement based on the vector field of the light source;
defining each optical surface of the optical system based on the vector field of the light source;
tracing a plurality of rays that propagates from the light source, traverses through the optical system and reaches a predetermined target area, wherein each of the plurality of rays is represented based on the vector field of the light source upon reflection, refraction, or transmission through or from each optical surface of the optical system; and
determining whether an illumination or an image characteristic at the predetermined target area meets one or more preset design requirements.

10. The apparatus of claim 9, wherein one or more of the optical surfaces are represented using spherical harmonics.

* * * * *